(12) United States Patent
Martin

(10) Patent No.: US 8,394,375 B2
(45) Date of Patent: Mar. 12, 2013

(54) ANTIBODIES FOR AMYLOID SPECIFIC PEPTIDES

(75) Inventor: Paul Taylor Martin, Bexley, OH (US)

(73) Assignee: The Regents of the University of California, Oakland, CA (US)

( * ) Notice: Subject to any disclaimer, the term of this patent is extended or adjusted under 35 U.S.C. 154(b) by 81 days.

(21) Appl. No.: 12/765,740

(22) Filed: Apr. 22, 2010

(65) Prior Publication Data

US 2010/0273233 A1 Oct. 28, 2010

Related U.S. Application Data

(62) Division of application No. 10/551,619, filed as application No. PCT/US2004/010939 on Apr. 7, 2004, now Pat. No. 7,745,569.

(60) Provisional application No. 60/461,168, filed on Apr. 7, 2003.

(51) Int. Cl.
*A61K 39/395* (2006.01)
*A61K 39/00* (2006.01)
*C12P 21/08* (2006.01)

(52) U.S. Cl. ............... 424/130.1; 424/141.1; 424/142.1; 424/135.1; 424/136.1; 424/178.1; 435/70.2; 530/388.1

(58) Field of Classification Search ........................ None
See application file for complete search history.

(56) References Cited

U.S. PATENT DOCUMENTS 6,090,589 A * 7/2000 Dimond et al. ............... 435/91.1
7,772,375 B2 * 8/2010 Greferath et al. ........ 530/388.85
2003/0194704 A1 * 10/2003 Penn et al. .................... 435/6

OTHER PUBLICATIONS

Rudikoff et al. Proc. Natl. Acad. Sci. USA 1982 vol. 79: p. 1979.*
Bard et al. Nature Medicine, 2000, 6: 916-919.*
Bajaj et al. "Ultra-Rare-Event Detection Performance of a Custom Scanning Cytometer on a Model Preparation of Fetal nBRCs" Cytometry, (2000).39:285-294.
Bowie et al., "Deciphering the Message in Protein Sequences: Tolerance to Amino Acid Substitutions," Science, 1990, 247:1306-1310.
Burgess et al., "Possible Dissociation of teh Heparatin-binding and Mitogenic Activities of Heparin-binding (Acidic Fibroblast) Growth Factor-1 from Its' Receptor-binding Activities by Site-directed Mutagenesis of a Single Lysine Residue," J. of Cell Bio., 1990, 111:2129-2138.
Cherny et al."Treatment with a Copper-Zinc Chelator Markedly and Rapidly Inhibits β-Amyloid Accumulation in Alzheimer's Disease Transgenic Mice". Neuron, (2001) 30:665-676.
Kang et al. "The precursor of Alzheimer's disease amyloid A4 protein resembles a cell-surface receptor" Nature, (1987). 325:733-736.
Kang et al. "Identification of peptides that specifically bind Aβ 1-40 amyloid in vitro and amyloid plaques in Alzheimer's disease brain using phage display" Neurobiology of Disease, (2003). 14:146-156.
Mazzuchcelli et al. "Cell-Specific Peptide Binding by Human Neutrophils" Blood, (1999). 93:1738.
Morris and Price "Pathologic Correlates to Nondemented Aging, Mild Cognitive Impairment, and Early-Stage Alzheimer's Disease" J. Mol. Neurosci., (2001). 17:101-118.
Parks et al."Neurotoxic Aβ peptides increase oxidative stress in vivo through NMDA-receptor and nitric-oxide-synthase mechanisms, and inhibit complex IV activity and induce a mitochondrial permeability transition in vitro" J. Neurochem., (2001). 76:1050-1060.
Roher et al. "Purification, ultrastructure, and chemical analysis of Alzheimer disease amyloid plaque core protein" Proc. Natl. Acad. Sci. USA, (1986). 83:2662-2666.
Selkoe "Alzheimer's Disease: Genes, Proteins, and Therapy" Physiol Rev, (2001). 81:741-766.
Smith and Scott "Libraries of Peptides and Proteins Displayed on Filamentous Phage" Methods. Enzymol., (1993). 217:228-257.
Stine et al. "The Nanometer-Scale Structure of Amyloid-β Visualized by Atomic Force Microscopy" J. Prot. Chem., (1996). 15:193-203.
Tucker et al. "The Plasmid System Is Induced by and Degrades Amyloid-β Aggregates" J. Neurosci., (2000). 20:3937-3946.
Watson et al. (1987). In Molecular Biology of the Gene, 4th ed., The Benjamin/Cummings Publ. Co., p. 224.

* cited by examiner

*Primary Examiner* — Chang-Yu Wang
(74) *Attorney, Agent, or Firm* — Joseph R. Baker, Jr.; Gavrilovich, Dodd & Lindsey LLP

(57) ABSTRACT

Phage peptide display technology was used to identify peptides that bind specifically to the amyloid form of the $A\beta_{1-40}$ peptide. Peptides with similar structural features and bind to the amyloid form of $A\beta_{1-40}$ but not to monomeric $A\beta_{1-40}$, are provided. Such peptides are useful as carrier molecules to deliver therapeutic and diagnostic reagents to amyloid plaques.

5 Claims, 8 Drawing Sheets

Potential Uses:
1. Conjugate to Neuroprotective agents
2. Conjugate to agents that destroy plaques
3. Conjugate to Inhibitors of plaque formation
4. Conjugate to plaque imaging agents
5. Anti-idiotype vaccine

_US 8,394,375 B2_

ANTIBODIES FOR AMYLOID SPECIFIC PEPTIDES

CROSS-REFERENCE TO RELATED APPLICATIONS

This application is a divisional of U.S. application Ser. No. 10/551,619, filed Apr. 26, 2007, which application is a U.S. National Stage Application filed under 35 U.S.C. §371 and claims priority to International Application Serial No. PCT/US2004/010939, filed Apr. 7, 2004, which claims priority from U.S. Provisional Application Set. No. 60/461,168, filed Apr. 7, 2003, which is incorporated herein by reference. U.S. application Ser. No. 10/551,619, filed Apr. 26, 2007, is U.S. Pat. No. 7,745,569 issued on Jun. 29, 2010.

STATEMENTS REGARDING FEDERALLY SPONSORED RESEARCH

This invention was made with government support under Grant No. NS37214 awarded by the National Institutes of Health. The government has certain rights in the invention.

TECHNICAL FIELD

This invention relates generally to peptides that interact with protein aggregates associated with a disease state, and more specifically to peptides that interact with amyloid plaques containing amyloid β(Aβ) peptide.

BACKGROUND

Alzheimer's disease (AD) is the major cause of dementia in the elderly, affecting approximately 3-4 million people in the United States alone. The decline of cognitive abilities in AD is associated with pathologic changes in the brain, the most prevalent of which are the formation of amyloid plaques and neurofibrilary tangles (Selkoe, Physiol. Rev. 81:741-766, 2001). Amyloid plaques in AD brains form at far greater numbers than in normal individuals. While amyloid plaques contain many proteins, they have as their principal constituent the 4 kDa amyloid-β (Aβ) peptide (Kang et al., Nature 325: 733-736. 1987). The formation of the Aβ peptide, and thereby Aβ amyloid, arises from aberrant processing of the amyloid precursor protein (APP). A number of studies support the idea that Aβ is itself neurotoxic, and therefore the high concentration of Aβ peptide in amyloid plaques may seed the generalized degeneration of neurons in surrounding areas (Morris and Price, J. Mol. Neurosci. 17:101-118, 2001).

One approach to inhibiting AD would appear to be to inhibit the proteases, in particular the K- and β-secretase, that produce the Aβ peptide. However, individuals without AD also have plaques, and as some Aβ peptide is produced in people without AD. Therefore, such peptide processing may be a byproduct of necessary protease functions and inhibiting APP processing may have unwanted and toxic consequences.

Another approach would be to design therapies that would either eliminate the toxic aspects of amyloid plaques or remove plaques from the brain altogether. For example, Aβ toxicity is associated with the generation of reactive oxygen species (Parks et al., J. Neurochem. 76:1050-1060, 2001) and with the accumulation of heavy metals (Cherny et al., Neuron 30:665-676, 2001). Therefore, the creation of a reducing or chelating environment locally at amyloid plaques may inhibit the toxicity associated with Aβ in these areas. Because many proteins in addition to Aβ accumulate in amyloid plaques, the activation of proteases may also aid in plaque removal or lessen plaque number or plaque size. Blocking of the cellular receptors that mediate Aβ toxicity in neurons may also have a therapeutic benefit.

These approaches would be greatly facilitated by the ability to target therapeutics directly to amyloid plaques. One way to do this would be to develop reagents that specifically bind Aβ amyloid and can be conjugated with therapeutic or diagnostic molecules. It is an object herein, among other objects, to provide reagents that specifically react with Aβ amyloid, diagnostic assays using such reagents, and methods for preparing reagents for identifying disease causing forms of other amyloid proteins and other disease-associated conformation dependent proteins.

SUMMARY

Provided herein are peptides that specifically react with a target polypeptide, which is the aberrant form of a polypeptide associated with a disease of protein aggregation (a disease involving a conformationally altered protein), such as amyloid diseases.

In one embodiment, an isolated polypeptide comprising the amino acid sequence Y (Trp/Phe) $Xaa_1$ $Xaa_2$ $Xaa_3$ $Xaa_4$ $Xaa_5$ (Trp/Phe) $Xaa_6$ $Xaa_7$ (Trp/Phe) Z (SEQ ID NO:17-20) is provided. Y, which may or may not be present, is a peptidic structure containing at least one cysteine residue and having the formula $(Xaa)_n$. Xaa is any amino acid residue and n is an integer from 1 to 20. Z, which may or may not be present, is a peptidic structure containing at least one cysteine residue and having the formula (Xaa), wherein Xaa is any amino acid residue and n is an integer from 1 to 20. The amino acid residues of in $Xaa_1$ through $Xaa_7$ can be any amino acid and the amino acid residues of $Xaa_1$ through $Xaa_5$ are positively charged.

In another embodiment, an isolated polypeptide comprising the amino acid sequence Y (Trp/Phe) $Xaa_1$ $Xaa_2$ $Xaa_3$ $Xaa_4$ $Xaa_5$ (Trp/Phe) $Xaa_6$ $Xaa_7$ $Xaa_8$ (Trp/Phe) Z (SEQ ID NO:21-24) is provided. Y, which may or may not be present, is a peptidic structure containing at least one cysteine residue and having the formula $(Xaa)_n$. Xaa is any amino acid residue and n is an integer from 1 to 20. Z, which may or may not be present, is a peptidic structure containing at least one cysteine residue and having the formula $(Xaa)_n$, wherein Xaa is any amino acid residue and n is an integer from 1 to 20. The amino acid residues of $Xaa_1$ through $Xaa_8$ is any amino acid, and at least two of the amino acid residues of $Xaa_1$ through $Xaa_5$ are positively charged.

In other embodiments, a is 1-15, 1-10, 1-5, or 1-3 residues in length. In addition, the cysteine in the Y peptidic structure and the cysteine in the Z peptidic structure are intramolecularly cross linked via a disulfide bond.

Isolated polypeptides comprising the amino acid sequence set forth in SEQ ID NO:2, SEQ ID NO:3, SEQ ID NO:4, SEQ ID NO:5 or SEQ ID NO:6, are provided. Isolated polypeptides consisting of the sequence set forth in SEQ ID NO:2, SEQ ID NO:3, SEQ ID NO:4, SEQ ID NO:5 or SEQ. ID NO:6, are also provided.

Nucleic acid sequences encoding a polypeptide of the invention are also provided. Vectors containing such nucleic acids, and cells containing such vectors, are also provided.

In addition, hybrid molecules, such as hybrid polypeptides, with such specificity are provided. The hybrid polypeptides include a peptide motif that specifically interacts with the target polypeptide (e.g., the amyloid form of the Aβ peptide) and that is inserted into a scaffold, such as a portion of an antibody or an enzyme or other suitable recipient, such that the resulting hybrid molecule specifically binds to conformation of the protein and not to another conformation of the protein (e.g., the amyloid form of the Aβ peptide and not the monomeric form of the Aβ peptide). Typically, the targeted conformation is the conformation involved in a disease. The polypeptide motif is inserted into the scaffold such that any desired function of the scaffold is retained and the inserted motif as presented retains it ability to specifically bind to the target. The selected scaffold can be exploited for its activities or binding sites to aid or permit detection of complexes between the motif and the target polypeptide. The scaffold can include, for example, neuroprotective agents to make amyloid plaques less toxic, amyloid destroying molecules to eliminate plaques, reagents that prevent amyloid plaque formation, or reagents useful for specifically imaging amyloid plaques in brain tissue.

Methods for producing peptides for detection or diagnosis of conformationally altered protein diseases and for treatment thereof are provided. Such diseases include, but are not limited to, Alzheimer's Disease (AD); Creutzfeldt-Jakob disease, including variant, sporadic and iatrogenic, scrapie and bovine spongiform encephalopathy; Type II Diabetes (islet amyloid peptide); Huntington's Disease; immunoglobulin amyloidosis; reactive amyloidosis associated with chronic inflammatory disease, e.g., inflammatory arthritis, granulomatous bowel disease, tuberculosis and leprosy; hereditary systemic amyloidosis associated with autosomal dominant inheritance of variant transthyretin (a.k.a., prealbumin) gene; ALS; Pick's Disease; Parkinson's disease; Frontotemporal dementia; Diabetes Type II; Multiple myeloma; Plasma cell dyscrasias; Familial amyloidotic polynueuropathy; Medullary carcinoma of thyroid; chronic renal failure; congestive heart failure; senile cardiac and systemic amyloidosis; chronic inflammation; atherosclerosis; familial amyloidosis and other such diseases.

The hybrid polypeptides can be used as reagents to detect the presence of the target polypeptide in a sample, such as a body fluid, tissue or organ or a preparation derived therefrom, and in drug screening assays to identify compounds that antagonize or agonize (i.e., modulate) the activity of a target polypeptide or that competitively inhibit interaction thereof with an infectious or disease-causing form of a target polypeptide, such as the amyloid form of Aβ peptide. The hybrid molecules also can be used as therapeutics. Since they specifically bind to a target polypeptide, they can be used to inhibit its activity, such as preventing or reducing the activity that results in protein aggregation or the conformation change leading to a deleterious effect. For example, as a therapeutic for treatment of diseases of protein aggregation a hybrid polypeptide can interrupt the polymerization or aggregation characteristic of disease pathogenesis.

In an exemplary embodiment, hybrid polypeptides that specifically react with the amyloid form of the amyloid β (Aβ) peptide are provided. In addition, hybrid polypeptides that bind specifically to disease-associated conformations of the Aβ peptide are provided.

In an exemplary embodiment, methods for detection of the amyloid form of the amyloid β (Aβ) peptide in a sample, such as a body fluid, tissue or organ from an animal, are provided. The methods are effected in solution phase or by providing the reagents or sample bound directly or indirectly to a solid support. Complexes between the reagents provided herein and the target polypeptides in the sample are detected.

Also provided are anti-idiotype antibodies (monoclonal or polyclonal) that are produced by immunizing a suitable animal with a peptide or antibody or fragment thereof that recognizes a peptide disclosed herein, monoclonal antibody Fab fragments or other inhibitory antibodies. Anti-idiotype antibodies raised against the combining sites of inhibitory antibodies or Fabs, can generate antibodies that recognize native the amyloid form of Aβ peptide. Such anti-idiotype antibodies can be used in all of the diagnostic, prognostic, therapeutic and screening methods that the hybrid polypeptides also provided herein are used. Methods for preparing such anti-idiotype antibodies by immunizing with a polypeptide or antibody or fragment thereof that recognizes the amyloid form of Aβ peptide from about amino acid 1 to amino acid 40, also are provided.

DESCRIPTION

Figure 1:
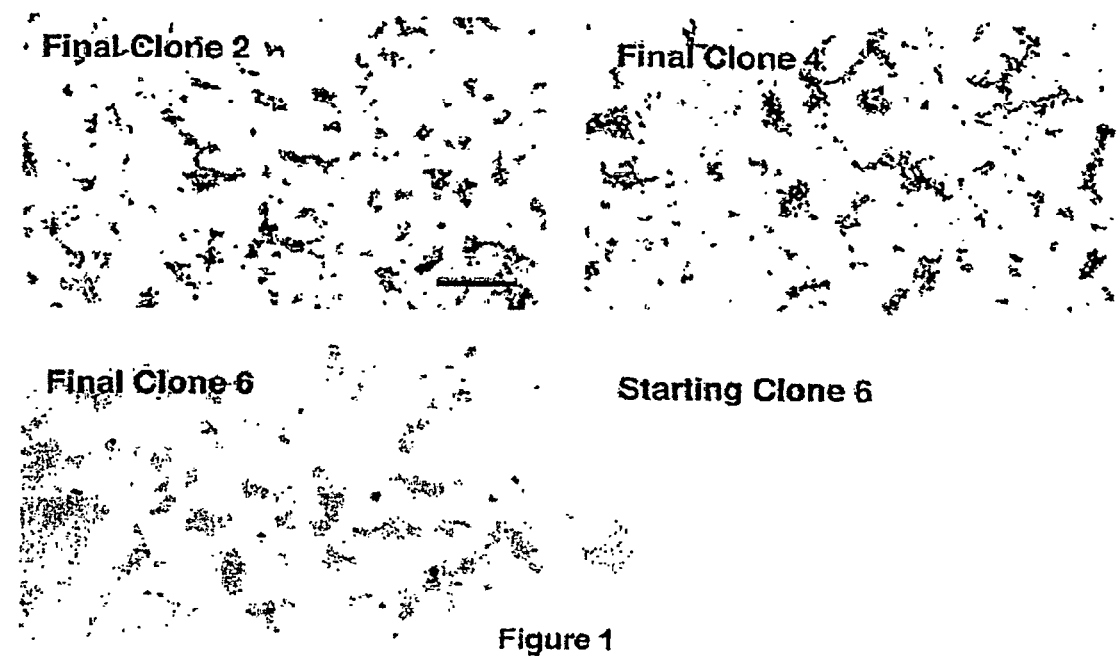
FIG. 1 depicts staining of amyloid $A\beta_{1-40}$ by phage peptides.

Peptides, nucleic acids encoding the peptides, and methods of using the peptides or nucleic acids to diagnose and/or treat diseases associated with plaque formation in brain tissue, such as Alzheimer's Disease (AD), are provided. For example, the peptides of the invention can specifically target the amyloid form of the $A\beta_{1-40}$ peptide in plaques of Alzheimer's patients.

Peptides

Provided herein are peptides that specifically bind to amyloid form of the Aβ peptide and methods of preparing such polypeptides and hybrid polypeptides that comprise a peptide of the invention and additional amino acids. The peptides of the invention bind to disease-causing conformers of conformationally altered protein diseases (diseases involving protein aggregation). As used herein, conformationally altered protein disease (or a disease of protein aggregation or a disease of protein conformation) refers to diseases associated with a protein or polypeptide that has a disease-associated conformation. Abnormal protein conformation, including, for example, misfolding and aggregation, can lead to a loss or alteration of biological activity. Abnormal protein conformation, including misfolding and aggregation is a causative agent (or contributory agent) in a number of mammalian, including, but are not limited to, Alzheimer's disease, prion spongiform encephaplopathies, such as bovine spongiform encephalopathy, scrapie of sheep, Kuru and Creutzfeldt-Jakob disease of humans, including variant, sporadic and iatrogenic, and amyotrophic lateral sclerosis (ALS).

In one embodiment, an isolated polypeptide comprising the amino acid sequence Y (Trp/Phe) $Xaa_1$ $Xaa_2$ $Xaa_3$ $Xaa_4$ $Xaa_5$ (Trp/Phe) $Xaa_6$ $Xaa_7$ (Trp/Phe) Z (SEQ ID NO:17-20) is provided. Y, which may or may not be present, is a peptidic structure containing at least one cysteine residue and having the formula $(Xaa)_n$. Xaa is any amino acid residue and n is an integer from 1 to 20. Z, which may or may not be present, is a peptidic structure containing at least one cysteine residue and having the formula $(Xaa)_n$, wherein Xaa is any amino acid residue and n is an integer from 1 to 20. The amino acid residues of in $Xaa_1$ through $Xaa_7$ can be any amino acid and the amino acid residues of $Xaa_1$ through $Xaa_5$ are positively charged.

In another embodiment, an isolated polypeptide comprising the amino acid sequence Y (Trp/Phe) $Xaa_1$ $Xaa_2$ $Xaa_3$ $Xaa_4$ $Xaa_5$ (Trp/Phe) $Xaa_6$ $Xaa_7$ $Xaa_8$ (Trp/Phe) Z (SEQ ID NO:21-24) is provided. Y, which may or may not be present, is a peptidic structure containing at least one cysteine residue and having the formula $(Xaa)_n$. Xaa is any amino acid residue and n is an integer from 1 to 20. Z, which may or may not be present, is a peptidic structure containing at least one cysteine residue and having the formula $(Xaa)_n$, wherein Xaa is any amino acid residue and n is an integer from 1 to 20. The amino acid residues of $Xaa_1$ through $Xaa_8$ is any amino acid, and at least two of the amino acid residues of $Xaa_1$ through $Xaa_5$ are positively charged.

In other embodiments, a is 1-15, 1-10, 1-5 or 1-3 residues in length. In addition, the cysteine in the Y peptidic structure and the cysteine in the Z peptidic structure are intramolecularly cross linked via a disulfide bond.

A "peptidic structure", as used herein, is an optional portion of a peptide or polypeptide comprising modified or unmodified amino acids. A peptidic structure contains at least one cysteine residue that can form a disulfide bond with another cystein residue. The cysteine residues contained in the Y or Z peptidic structures can be positioned anywhere within the structure as long as they can form a disulfide bond.

Isolated polypeptides comprising the amino acid sequence set forth in SEQ ID NO:2, SEQ ID NO:3, SEQ ID NO:4, SEQ ID NO:5 or SEQ ID NO:6, are provided. Isolated polypeptides consisting of the sequence set forth in SEQ ID NO:2, SEQ ID NO:3, SEQ ID NO:4, SEQ ID NO:5 or SEQ ID NO:6, are also provided.

Peptides and polypeptides of the invention include those containing conservative amino acid substitutions. Such peptides and polypeptides are encompassed by the invention provided the peptide or polypeptide can bind to the amyloid form of Aβ peptide. As used herein, suitable conservative substitutions of amino acids are known to those of skill in this art and can be made generally without altering the biological activity of the resulting molecule. Those of skill in this art recognize that, in general, single amino acid substitutions in non-essential regions of a polypeptide do not substantially alter biological activity (see, e.g., Watson et al. Molecular Biology of the Gene, 4th Edition, 1987, The Benjamin/Cummings Pub. co., p. 224). Such substitutions can be made in accordance with those set forth in TABLE 2 as follows: Ala (A) Gly; Ser Arg (R) Lys Asn (N) Gln (SEQ ID NO:25); H is Cys (C) Ser Gln (O) Asn Glu (E) Asp Gly (G) Ala (SEQ ID NO:26); Pro H is (H) Asn; Gln Ile (I) Leu; Val Leu (L) Ile; Val Lys (K) Arg; Gln; Glu Met (N) Leu; Tyr; Ile Phe (F) Met; Leu; Tyr Ser (S) Thr Thr (T) Ser Trp (W) Tyr Tyr (Y) Trp (SEQ ID NO:27); Phe Val (V) Ile; Leu.

Other substitutions also are permissible and can be determined empirically or in accord with known conservative substitutions.

Provided are peptides and polypeptides that preferentially (specifically) bind to one conformer (generally the disease-associated conformer) with greater affinity, typically at least 0.5, 1, 2, 3, 5, 10-fold or greater, than to the other conformer. Also contemplated are peptides-containing deletions of one or more amino acids that result in the modification of the structure of the resultant molecule but do not significantly altering its ability to bind to one conformer, such as amyloid form of the Aβ peptide, to form a plaque-protein complex.

Nucleic Acid Molecules

Nucleic acid molecules encoding any of the peptides, polypeptides or hybrid polypeptides provided herein are provided. Such molecules can be introduced into plasmids and vectors for expression in suitable host cells.

As used herein, the term "nucleic acid" refers to single-stranded and/or double-stranded polynucleotides such as deoxyribonucleic acid (DNA), and ribonucleic acid (RNA) as well as analogs or derivatives of either RNA or DNA. Also included in the term "nucleic acid" are analogs of nucleic acids such as peptide nucleic acid (PNA), phosphorothioate DNA, and other such analogs and derivatives or combinations thereof. The term should be understood to include, as equivalents, derivatives, variants and analogs of either RNA or DNA made from nucleotide analogs, single (sense or antisense) and double-stranded polynucleotides. Deoxyribonucleotides include deoxyadenosine, deoxycytidine, deoxyguanosine and deoxythymidine. For RNA, the uracil base is uridine.

Plasmids and vectors containing the nucleic acid molecules also are provided. Cells containing the vectors, including cells that express the encoded proteins are provided. The cell can be a bacterial cell, a yeast cell, a fungal cell, a plant cell, an insect cell or an animal cell. Methods for producing a hybrid polypeptide, for example, growing the cell under conditions whereby the encoded polypeptide is expressed by the cell, and recovering the expressed protein, are provided herein. The cells are used for expression of the protein, which can be secreted or expressed in the cytoplasm. The hybrid polypeptides also can be chemically synthesized using standard methods of protein synthesis.

Hybrid Molecules

For disease of protein conformation the same protein (or a portion thereof) exhibits more than one isoform (conformer) such that at least one form is causative of a disease, such as the amyloid form of the Aβ peptide, or is involved in the disease. For purposes of diagnosis, prognosis, therapy and or drug screening it is advantageous to have molecules that specifically interact (i.e. react with greater affinity, typically at least, 2-, 5-10-fold, generally at least about 100-fold) with a disease-associated conformer than with a benign (non-disease involved) conformer (or vice versa). Hence provided herein are peptides that specifically react with one conformer of a protein (i.e., the amyloid form of the Aβ peptide). Typically the molecules interact with a disease-associated conformer. A hybrid molecule of the invention includes a peptide or polypeptide that binds to the amyloid form of Aβ peptide, and a scaffold molecule. The scaffold molecule can include a diagnostic or therapeutic reagent. The therapeutic or diagnostic reagent can be a polypeptide, small molecule or compound.

In particular, provided herein are hybrid molecules, such as hybrid polypeptides, that include a peptide or polypeptide provided herein, and additional amino acid residues (typically, 5, 10, 15, 20, 30, 40, 50, 100 or more) such that the resulting hybrid molecule specifically interacts with the amyloid form of the Aβ peptide). The motif can be modified, such as by replacing certain amino acids or by directed and random evolution methods, to produce motifs with greater affinity.

As used herein, a hybrid polypeptide refers to a polypeptide that includes regions from at least two sources, such as from an antibody or enzyme or other scaffold that can be a recipient, and a binding motif, such as a polypeptide or peptide that binds to an amyloid form of the Aβ peptide.

Thus, among the hybrid molecules provided herein are hybrid molecules, particularly hybrid polypeptides, that are produced by grafting a binding motif (e.g., peptide) from one molecule into a scaffold, such as an antibody or fragment thereof or an enzyme or other reporter molecule. The hybrid polypeptides provided herein, even the hybrid immunoglobulins, are not antibodies per se, but are polypeptides that are hybrid molecules containing a selected motif (e.g., a peptide that binds to the amyloid form of the Aβ peptide) inserted into another polypeptide such that the motif retains or obtains the ability to bind to a protein involved in disease of protein aggregation. The hybrid polypeptides can include portions of antibodies or other scaffolds, but they also include a non-immunoglobulin or non-scaffold portion grafted therein. The non-immunoglobulin portion is identified by its ability to specifically bind to a targeted polypeptide isoform. The hybrid polypeptide can specifically bind to the targeted infectious or disease-related or a selected isoform of a polypeptide as monomer with sufficient affinity to detect the resulting complex or to precipitate the targeted polypeptide.

The scaffold is selected so that insertion of the motif therein does not substantially alter (i.e., retains) the desired binding specificity of the motif. The scaffold additionally can be selected for its properties, such as its ability to act as a reporter.

Methods for production of hybrid molecules that specifically interact with a one form of a conformer of a protein associated with a disease of protein conformation or involving protein aggregation are provided. In these methods a polypeptide motif from the protein is inserted into a scaffold such that the resulting molecule exhibits specific binding to one conformer compared to other conformers. In particular, the hybrid molecule can exhibit specific binding to the amyloid form of the Aβ peptide.

Peptides of the invention have been shown to bind to AD plaques in vitro and in vivo. The peptides can be incorporated in to a scaffold that comprises additional amino acid sequences and/or compounds. The hybrid molecule can then be used to label or treat the plaques associated with Aβ amyloid. The polypeptides, nucleic acids encoding the polypeptides, and methods of using the polypeptides or nucleic acids can be used to identify, diagnose and/or treat disorders associated with plaque formation in brain tissue.

Any molecule, such as a polypeptide, into which the selected polypeptide motif is inserted (or linked) such that the resulting hybrid polypeptide has the desired binding specificity, is contemplated for use as part of the hybrid molecules herein. The polypeptides can be inserted into any sequence of amino acids that at least contains a sufficient number (10, 20, 30, 50, 100 or more amino acids) to properly present the motif for binding to the targeted amyloid plaque. The purpose of the scaffold is to present the motif to the targeted polypeptide in a form that binds thereto. The scaffold can be designed or chosen to have additional properties, such as the ability to serve as a detectable marker or label or to have additional binding specificity to permit or aid in its use in assays to detect particular isoforms of a target protein (e.g., the amyloid form of the Aβ peptide) or for screening for therapeutics or other assays and methods.

The scaffolds include reporter molecules, such as fluorescent proteins and enzymes or fragments thereof, and binding molecules, such as antibodies or fragments thereof. Selected scaffolds include all or portions of antibodies, enzymes, such as luciferases, alkaline phosphatases, β-galactosidase and other signal-generating enzymes, chemiluminescence generators, such as horseradish peroxidase; fluorescent proteins, such as red, green and blue fluorescent proteins, which are well known; and chromogenic proteins.

The peptide motif is inserted into the scaffold in a region that does not disturb any desired activity. The scaffolds can include other functional domains, such as an additional binding site, such as one specific for a second moiety for detection.

Diagnostic and Therapeutic Methods

Methods for detecting an isoform of polypeptide associated with a disease of protein aggregation are provided. The methods include the steps of contacting a sample suspected of containing the isoform with a hybrid polypeptide that specifically binds to the isoform, such as the amyloid form of Aβ peptide, and detecting binding of the polypeptide. Detection can be effected by any method known to those of skill in the art, including radiolabel, color or fluorescence detection, mass spectrometry and other detection methods. For example, the hybrid polypeptide can be detectable labeled or can contain a fluorescent or chromogenic moiety or moieties or can be a fluorescent or chromogenic peptide or other reporter, such as an enzyme, including a luciferase (from Renilla, Aequora and from other deep sea creatures, from bacteria or insects) or other enzymatic label. Alternatively, a label, such as a fluorescent protein or enzyme can serve as a scaffold into which the motif is inserted, such that the enzymatic activity or fluorescence is retained. Also, the hybrid polypeptide can include additional binding sites to capture antibodies or nucleic acids or other detectable moieties.

In one embodiment, a method for identifying the disease-causing form of a target polypeptide in cells is provided. The hybrid polypeptide specific for the target is detectably labeled, such as fluorescently labeled or inserted into a fluorescent protein or a luciferase, and contacted with a sample, such as a blood sample. Labeled cells are identified, such as by flow cytometry and scanning cytometry. Methods and instruments for identifying very low concentrations of labeled cells among unlabeled cells are available (see, e.g., Bajaj et al. (2000) Cytometry 39:285-294, published U.S. application Ser. No. 09/123,564, published as US2002018674, and instrumentation commercialized by Q3DM, LLC, San Diego). In an alternative embodiment, label the hybrid polypeptides that interact with distinct epitopes, such as hybrid polypeptides containing residues from 136-158 and 89-112, with different color dyes. The resulting labeled hybrid polypeptides, such as two polypeptides, are mixed with cells to be tested simultaneously or sequentially. Association of both colors with a single cell, provides a self-confirmatory assay. For example, peptides that bind to the amyloid form of Aβ peptide (or portions thereof sufficient to interact with an epitope, such as at least amino acids 1-40 of the Aβ peptide, are grafted into for into different florescent protein, such as a green fluorescent proteins with distinct emission spectra will achieve the same double labelling of single cells.

Diseases diagnosed or detected include amyloid diseases such as, Alzheimer's Disease, Type II Diabetes, Huntington's Disease, immunoglobulin amyloidosis, reactive amyloidosis associated with chronic inflammatory disease, e.g., inflammatory arthritis, granulomatous bowel disease, tuberculosis and leprosy, hereditary systemic amyloidosis associated with autosomal dominant inheritance of variant transthyretin gene, ALS, Pick's Disease, Parkinson's disease, Frontotemporal dementia, Diabetes Type II, Multiple myeloma, Plasma cell dyscrasias, Familial amyloidotic polynueuropathy, Medullary carcinoma of thyroid; chronic renal failure, congestive heart failure, senile cardiac and systemic amyloidosis, chronic inflammation, atherosclerosis and familial amyloidosis.

EXAMPLES

A phage peptide library encoding $5 \times 10^7$ random 20 amino acid sequences was used to pan for binding to $A\beta_{1-40}$ amyloid and against adherence to tissue culture plastic. We decided to use a library that would be cysteine cross-linked at its base so as to increase the chance that the inserted peptide would have some tertiary structure. In addition, even though phage libraries with larger peptide inserts contain fewer of the total number of possible peptide combinations, we surmised that longer sequences would be required to identify high affinity binding motifs for the 40 amino acid Aβ peptide. After three rounds of positive panning against the amyloid form of the $A\beta_{1-40}$ peptide, and two rounds of negative panning against tissue culture plastic, ten individual clones were sequenced and compared these to ten randomly picked sequences from the starting library (Table 1). Multiple clones of only two phage sequences that adhered to the $A\beta_{1-40}$ amyloid were identified.

The identified sequences had 3-fold more bulky hydrophobic residues (phenylalanine or tryptophan) than did sequences randomly picked from the starting library. Selected sequences shared bulky hydrophobic amino acids that were spaced at even intervals [(W/F) $X_5$(W/F)$X_{2/3}$(W/F)] (SEQ ID NOs: 1 and 33, respectively), and had two positively charged residues (and no negatively charged residues) in the $X_5$ region.

Clones expressing the DWGKGGRWRLWPGASGKTEA (SEQ ID NO:2) sequence stained $A\beta_{1-40}$ amyloid. In contrast, phage clones containing the PGRSPFTGKKLFNQEFSQDQ (SEQ ID NO:3) sequence stained $A\beta_{1-40}$ amyloid less well, but the level of staining was still significantly above background levels. No clones from the starting library stained any $A\beta_{1-40}$ aggregates when used at the same concentration, and no signal was observed in the absence of phage with secondary antibody alone. In addition, no phage clones stained monomeric peptide that had been immobilized on nitrocellulose. The Aβ aggregates identified by these peptides are larger than individual 2-12 nm Aβ fibrils and more closely resemble large (1-10 μm) aggregates found in amyloid plaques (Roper et al., Proc. Natl. Acad. Sci. USA 83:2662-2666, 1986) and in some preparations of $A\beta_{1-40}$ (Stine et al., J. Prot. Chem. 15:193-203, 1996).

Figure 2:
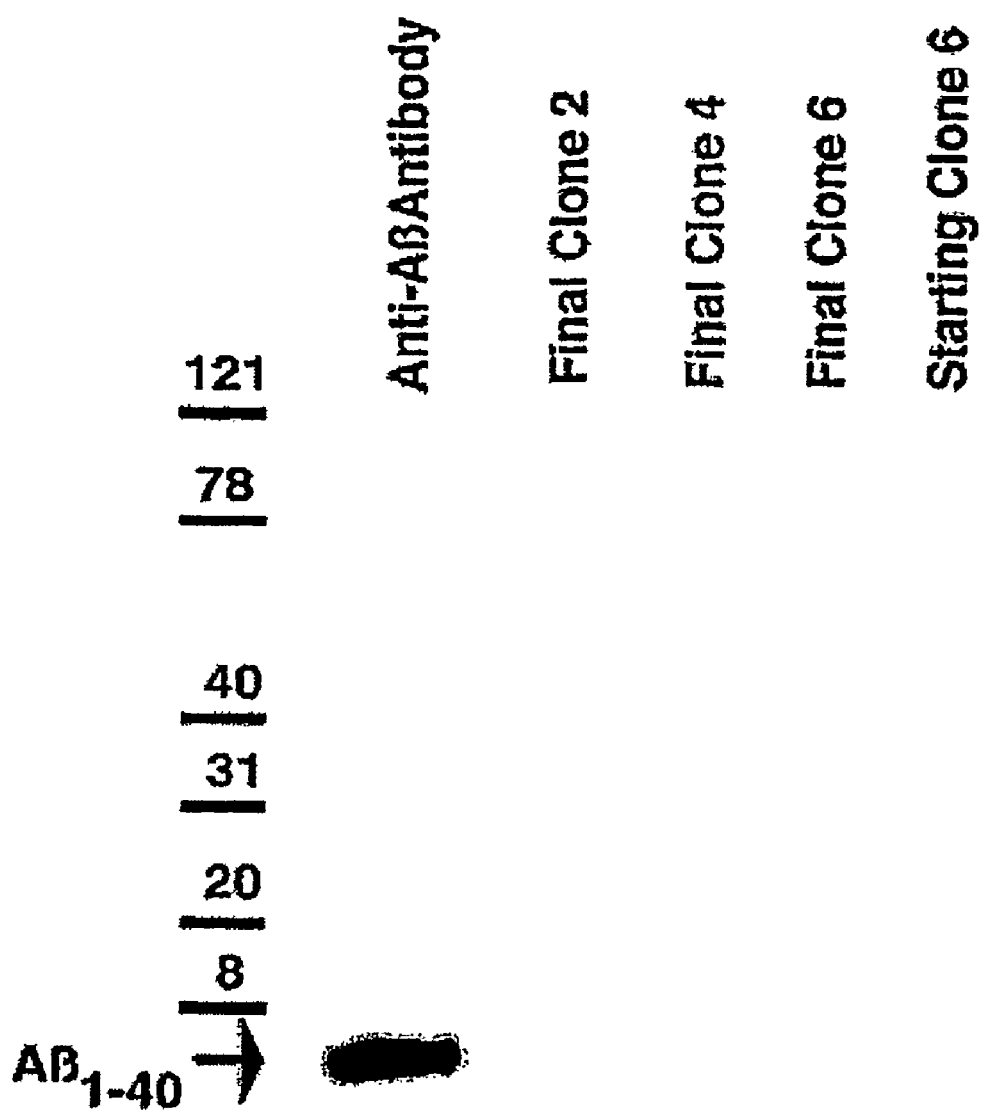
FIG. 2 depicts immunoblotting of monomeric $A\beta_{1-40}$ by phage peptides.

No clones expressing peptides from either the starting or the final peptide sequences identified monomeric $A\beta_{1-40}$ (FIG. 2). Monoclonal antibodies to Aβ peptide did bind, however, demonstrating proper transfer of the Aβ peptide to nitrocellulose. The lack of staining or blotting of the isolated phage sequences to linear $A\beta_{1-40}$ peptide indicate that they specifically recognize the amyloid form of $A\beta_{1-40}$.

To verify that the DWGKGGRWRLWPGASGKTEA (SEQ ID NO:2) peptide would identify $A\beta_{1-40}$ amyloid independently of its presence in bacteriophage, this peptide was produced in recombinant form as a fusion protein with thioredoxin. Cysteines were engineered at either end of the peptide in the fusion construct, along with several other residues from the phage coat protein. The ultimate or penultimate residue was engineered to be a proline to mimic predicted beta turn at either side of the 20 amino acid insert. This protein was termed Thio-Aβ. Recombinant thioredoxin without the Aβ-peptide binding sequence was termed Thio.

Figure 3:
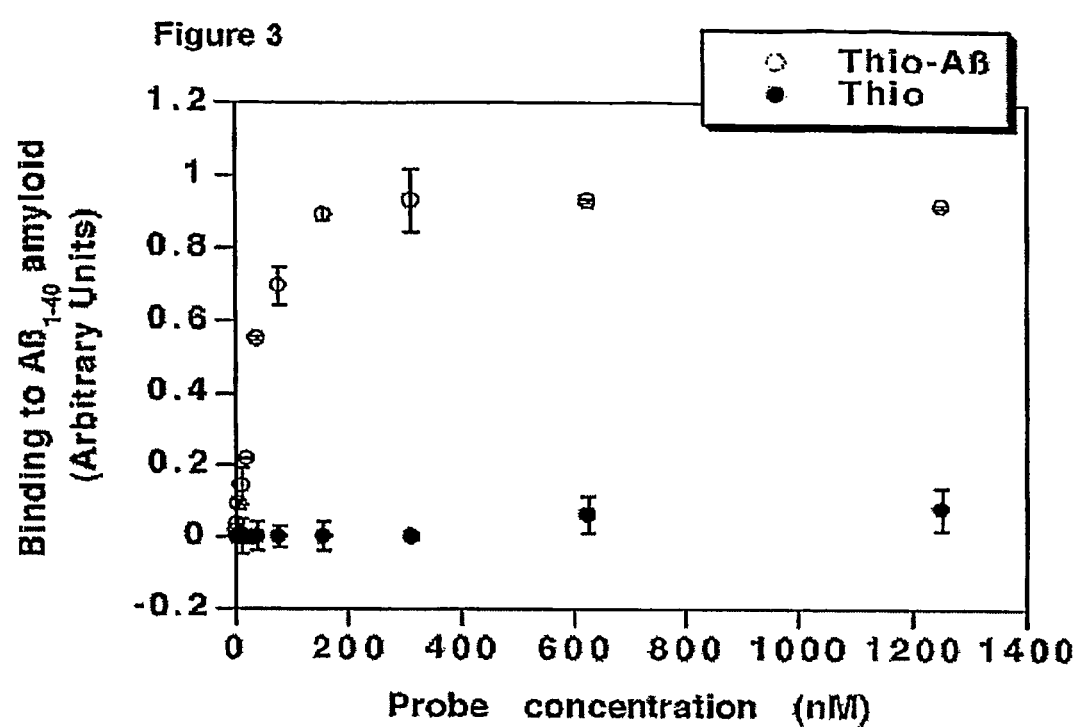
FIG. 3 depicts recombinant Aβ-binding peptide binding with high affinity to $A\beta_{1-40}$ amyloid in vitro.

After purification by nickel resin chromatography, binding studies were performed on Thio and Thio-Aβ to immobilized $A\beta_{1-40}$ amyloid (FIG. 3). Thio did not bind to $A\beta_{1-40}$ amyloid at any concentration below 200 μM. In contrast, Thio-Aβ bound with high affinity to $A\beta_{1-40}$ amyloid. A Kd of 60 nM was measured and binding was saturating at 200 nM. To determine if Thio-Aβ would bind to Aβ amyloid that was present in the amyloid plaques found in Alzheimer's disease (AD) brains (FIG. 4), AD and normal brains were stained with Thio and Thio-Aβ. Thio-Aβ bound specifically to amyloid plaques in AD brains, while it did not bind to normal brain samples. Staining of neurofibrillary tangles was not evident. Positive staining of amyloid plaques with Thio-Aβ was seen in AD brains from multiple subjects and was absent in sections from several normal brain samples. Concentrations as low as 100 nM yielded positive staining for Thio-Aβ. In contrast, Thio did not bind to either normal or AD brain at any of the concentrations used.

Figure 5:
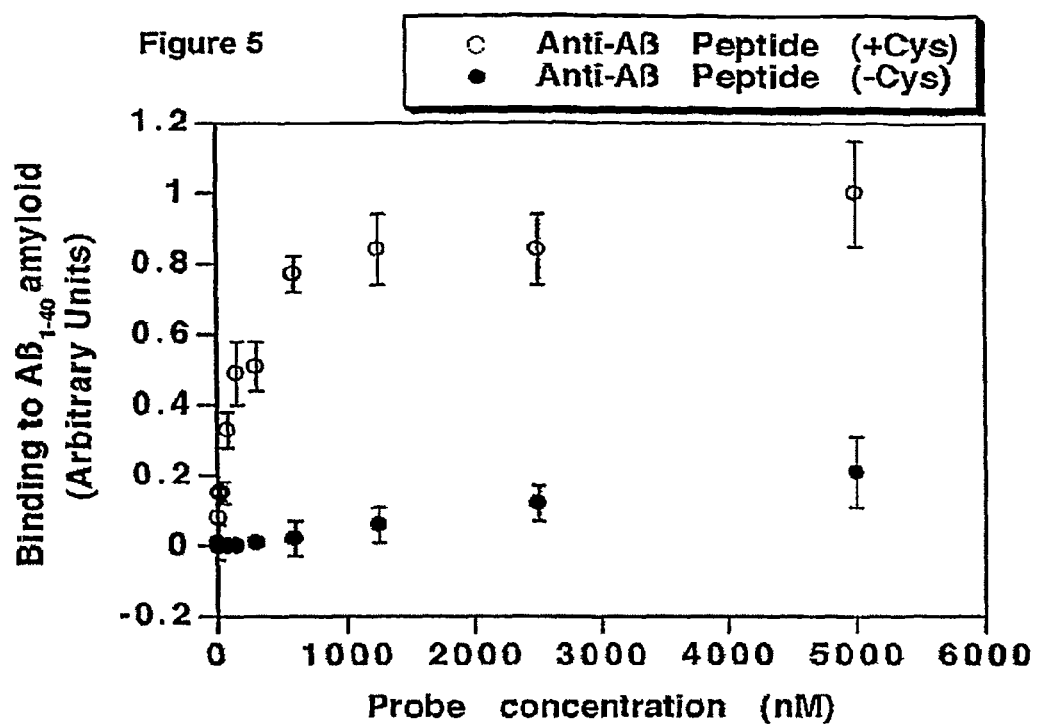
FIG. 5 depicts binding of synthetic peptides to $A\beta_{1-40}$ amyloid in vitro.

Chemically synthesized peptides were tested to identify binding to $A\beta_{1-40}$ amyloid (FIG. 5). To test the relative contribution of the flanking (N-terminal and C-terminal) cysteines, peptides were synthesized that either had or did not have these residues; Both peptides were made with an N-terminal biotin label to allow identification using streptavidin. Biotin-DWGKGGRWRLWPGASGKTEA (SEQ ID NO:2) and Biotin-AECDWGKGGRWRLWPGASGKTEACGP (SEQ ID NO:4) were tested for binding to amyloid $A\beta_{1-40}$. Biotin-AECDWGKGGRWRLWPGASGKTEACGP (SEQ ID NO:4) bound $A\beta_{1-40}$ amyloid with a Kd of 320 nM. Biotin-DWGKGGRWRLWPGASGKTEA (SEQ ID NO:2), which lacks flanking cysteines, showed binding in the 10-80 μM range. These data indicate that the terminal cysteines, which can form a disulfide bond, induce a conformation of the 20 amino acid insert that enhances high affinity binding to $A\beta_{1-40}$ amyloid.

Figure 6:
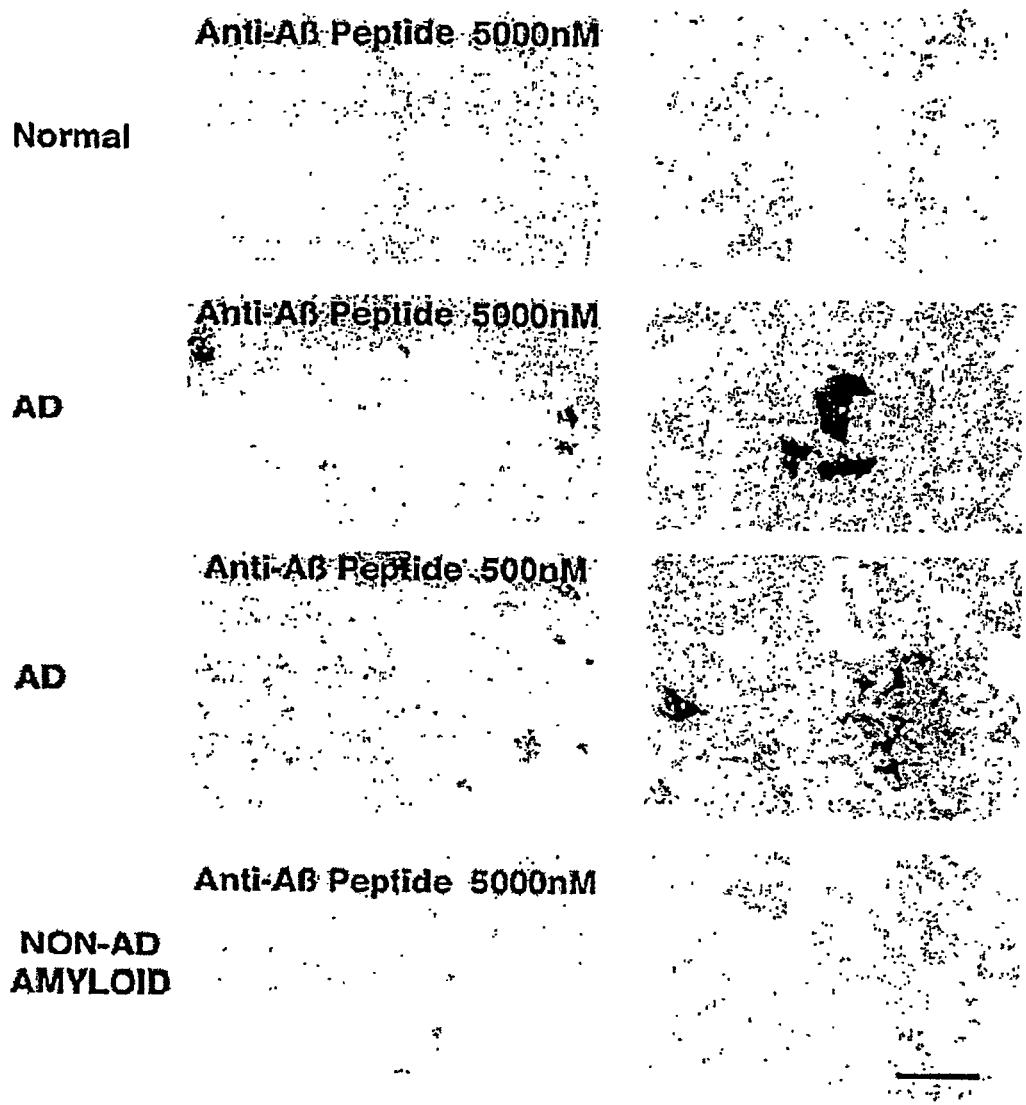
FIG. 6 depicts specific staining amyloid plaques in Alzheimer's disease brain with a synthetic peptide.

Staining of AD and non-AD brain was repeated using Biotin-AECDWGKGGRWRLWPGASGKTEACGP (SEQ ID NO:4) (FIG. 6). In addition, tissue from organs (kidney, brain, large bowel, small bowel, and prostate) from a non-AD patient with amyloidosis were stained. As with Thio-Aβ, the synthetic peptide specifically stained amyloid plaques in AD brain. No staining of neurofibrillary tangles was detected. As with binding to $A\beta_{1-40}$ amyloid in vitro, slightly higher concentrations were needed for staining of plaques relative to Thio-Aβ. Concentrations as low as 500 nM gave good staining with the peptide. Simultaneous staining of kidney sections containing non-Aβ amyloid demonstrated that binding was specific for Aβ amyloid. Thus, this peptide sequence is a high affinity probe for Aβ amyloid both in vitro and in vivo, both within and outside the context of other recombinant protein sequences.

Using phage display, at least two cysteine-linked 20 amino acid peptide sequences that bind to the amyloid form of $A\beta_{1-40}$ have been identified. Neither of these sequences bind monomeric $A\beta_{1-40}$, and therefore these peptides specifically identify the amyloid form of the $A\beta_{1-40}$ protein. Both of these sequences share a [(W/F)$X_5$(W/F) $X_{2/3}$ (W/F)] (SEQ ID NOs:1 and 33, respectively) structure in common, and both have two positively charged (and no negatively charged) amino acids within the $X_5$ region. Therefore, cysteine-linked peptides with this repeating hydrophobic motif provides a template for the design of other peptides that can bind to Aβ amyloid with even higher affinity. Production and purification of one of these peptide sequences as a fusion protein with thioredoxin (Thio-Aβ), or direct chemical synthesis of the peptide, created a high affinity binding protein for $A\beta_{1-40}$ amyloid in vitro. These reagents also bound specifically to amyloid plaques in Alzheimer's disease (AD) brain.

Applications for peptides (FIG. 7) of the invention include synthesizing hybrid molecules comprising such peptides and a scaffold. The scaffold can include: 1) molecules designed to inhibit the toxicity of amyloid plaques; 2) anti-oxidants to protect against oxidative damage caused by the Aβ peptide or to chelators that could inhibit the accumulation of toxic metals; 3) reagents that degrade plaques such as activators of tissue plasminogen, urokinase-type plasminogen, or matrix metalloproteases that stimulate the breakdown of amyloid plaque proteins (Tucker et al., J. Neurosci. 20:3937-3946, 2000); 4) reagents that inhibit plaque formation; 5) radionuclides or other markers to image amyloid plaques in living patients. Alzheimer's disease is currently diagnosed through cognitive measures on patient interview. These measures are time consuming, and post-mortem analysis of brains is currently required for a definitive diagnosis. Thus, there is no way to measure to extent of brain pathology in living patients. Such a lack of a quantitative measure makes it difficult to diagnose the early stages of the disease and to make determinations as to the efficacy of various treatments.

These peptides of the invention can also be used to develop an anti-idiotype vaccine. Since these peptides bind Aβ amyloid, they may mimic the Aβ amyloid binding site of cellular receptors involved in mediating the neurotoxic effects of Aβ. If so, immunization using these peptides could stimulate the production of blocking antibodies to cellular binding sites for Aβ amyloid.

Thus, the invention also provides are anti-idiotype antibodies (monoclonal or polyclonal) that are produced by immunizing a suitable animal with a polypeptide or antibody or fragment thereof that recognizes the a peptide of the invention. Anti-idiotype antibodies raised against the combining sites of inhibitory antibodies or Fabs can generate antibodies that recognize native a peptide that binds to the amyloid form of Aβ peptide.

Such anti-idiotype antibodies can be used in all of the diagnostic, prognostic, therapeutic and screening methods that the hybrid polypeptides also provided herein are used. Methods for preparing such anti-idiotype antibodies are known to those skilled in the art.

The development of small peptides that bind to Aβ may be superior for the diagnostic and treatment purposes to other molecules that are known to bind to Aβ peptide. The molecules that can bind to Aβ amyloid can be broken down into three groups: non-antibody proteins, antibodies, and small organic molecules. As the peptide sequences identified herein are small and relatively hydrophobic, they can traverse the blood-brain barrier efficiently. In addition, these peptides are less likely to have any significant toxicity when compared with small organic molecules and may in some instances be easier to conjugate with other reagents.

A cysteine-linked phage peptide library encoding $5 \times 10^7$ random 20 amino acid insertions was obtained. $A\beta_{1-40}$ peptide (DAEFKHDSGTEVHHQKLVFFAEDVGSNKGAIIGLMVGGVV) (SEQ ID NO:28) was purchased from Bachem (Torrence, Calif.). Biotinylated anti-sheep M13 phage polyclonal antibody was purchased from 5 Prime-3 Prime (Boulder, Colo.). Alkaline phosphatase and horseradish peroxidase coupled streptavidin were purchased from Boehringer Mannheim (Indianapolis, Ind.) and Jackson Immunochemicals (West Grove, Pa.). Radionucleotides for DNA sequencing were purchased from Amersham (Piscataway, N.J.). Oligonucleotides were purchased from Genosys (The Woodlands, Tex.). Recombinant peptides fused to thioredoxin were made and purified using plasmids and reagents in the His-Patch ThioFusion expression system from Invitrogen (Carlsbad, Calif.). Anti-Aβ monoclonal antibody (2066) was a generous gift from Edward Koo (UC San Diego). Synthetic peptides containing an N-terminal biotin were synthesized and purified by AnaSpec (San Jose, Calif.).

Phage panning and quantitation: Methods for phage panning and amplification were performed as described by Mazzuchcelli et al. (Blood 93:1738, (1999)). $A\beta_{1-40}$ peptide was added at a concentration of 20 μg/ml in Tris-buffered saline (TBS pH 7.4) to wells of a 24 well tissue culture plate (Falcon-Becton Dickinson, Franklin Lakes, N.J.). Numerous amyloid fibrils and aggregates were evident on the bottom of the plate after several days (Stine et al., J. Prot. Chem. 15:193-203 (1996)), however, peptide was left on for five days to allow more complete aggregation of the peptide to its amyloid form. Round 1: Plates were washed with phage buffer (Hanks balanced salts with 1 mM $CaCl_2$ and 1 mM $MgCl_2$, 10 mM Hepes, pH. 7.4, and 0.5% BSA) 3 times for 5 minutes each. Both plates were then incubated with 15 μl (5-10 copies of every sequence) of starting library diluted into 300 μl of phage buffer for one hour with rocking on a shaker. Plates were washed 6 times for 5 minutes each with phage buffer, and bound phage were eluted with phage buffer containing 0.5% Tween 20. Eluted phage were incubated with starved K91 cells for 15-20 minutes at room temperature and grown in Luria Broth (LB) with 1 μg/ml kanamycin for 45 minutes on a bacterial shaker. A portion of this material was used to titer phage using a plaque assay as previously described (Smith and Scott, Methods. Enzymol. 217:228-257 (1993)). Infected bacteria were then plated on 15 cm LB-agar plates containing 75 μg/ml kanamycin overnight at 37° C. Bacteria were scraped from plates and collected in 3 ml TBS per plate (pH 7.5). Bacterial suspension was transferred to Nalgene tubes and spun at 9,100 g for 10 minutes. Supernatant was collected and phage precipitated in 0.15 volumes of PEG/NaCl (16.7% polyethylene glycol-8000/3.3M NaCl) on ice for two hours. Precipitated phage was spun at 9,100 g at 4° C. for 30 minutes and re-suspended in 150 mM NaCl, 10 mM HEPES pH 7.4. Phage were then re-precipitated as above and suspended in 150 mM NaCl, 10 mM HEPES pH 7.4. Rounds 2 and 3: Amplified phage from Round 1 was incubated on a tissue culture well without $A\beta_{1-40}$ peptide for one hour in phage buffer. Supernatant from this well was then incubated on a plate coated with amyloid $A\beta_{1-40}$ as in Round 1. All other procedures were done as described in Round 1.

DNA sequencing of phage clones: At the end of Round 3 of panning, phage-infected $K_{91}$ cells were diluted and plated as single colonies on LB-Agar plates with 75 μg/ml kanamycin. Individual colonies were grown up at 37 C for 12 hours in LB with 1 μg/ml kanamycin. Bacteria were spun down at 10,000 g for five minutes, after which the supernatant was precipitated in PEG/NaOAc (3.6%/450 mM) for 24 hours on ice. Precipitated phage DNA was isolated by spinning at 10,000 g for 15 minutes and re-suspended in Tris-EDTA (TE, pH 7.5). Anti-phage primer was added (5' gtttgtcgtctttccagacg) (SEQ ID NO:29) and DNA sequencing reactions were run using the Sequence sequencing kit (Amersham, Piscataway, N.J.).

Staining and blotting with phage: $10^{11}$ PFU (plaque forming units)/ml of various phage clones were incubated with the amyloid form of $A\beta_{1-40}$ peptide. Aβ amyloid was made by incubating peptide in TBS (pH 7.4) for 7 days on Falcon 24-well tissue culture wells. After washing, bound phage were visualized by incubation with biotinylated anti-M13 antibody and alkaline phosphatase-conjugated streptavidin, followed by incubation for equivalent times in 5-bromo-4-chloro-3-indolyl phosphate (BCIP) and nitroblue tetrazolium (NBT). No staining was seen with any phage on control plates lacking $A\beta_{1-40}$.

Phage were also used to stain monomeric and amyloid forms of $A\beta_{1-40}$ peptide that had been immobilized on nitrocellulose. The linear and amyloid forms of Aβ were made as previously described (Tucker et al., 2000) and immobilized nitrocellulose-coated tissue culture plates, also as previously described (Martin and Sanes, 1997). Phage clones selected to bind the amyloid form of $A\beta_{1-40}$ did not bind non-amyloid $A\beta_{1-40}$. For immunoblotting, 10 ng of monomeric $A\beta_{1-40}$ was separated on a 4-12% Bis/Tris NuPAGE gradient gel (Novex; San Diego, Calif.). After transfer to nitrocellulose, blots were blocked in phage buffer and incubated with $10^{11}$ PFU/ml of each clone. After washing in phage buffer (without BSA), blots were incubated with biotinylated anti-M13 antibody followed by streptavidin-coupled horseradish peroxidase. Blots were developed using the ECL chemiluminescence method (Pierce, Madison Wis.). $A\beta_{1-40}$ peptide was also blotted with a monoclonal antibody that recognizes the $A\beta$ peptide to confirm protein transfer.

Production of recombinant $A\beta$-binding peptide:
Complementary oligonucleotides encoding the DWGKG-GRWRLWPGASGKTEA (SEQ ID NO:2) peptide sequence were annealed, digested with Kpn I and Xba I, and ligated into pThioHisC plasmid (Invitrogen; Carlsbad, Calif.) at the Kpn I and Xba I sites using the following sequences:

```
                                        (SEQ ID NO: 30)
5' CGGGGTACCTGCAGAATGCGATTGGGGGAAGGGGGGTC

GGTGGCGGTTGTGGCCGGGTGCGTCGGGGAAGACGGAGGCG

TGCGGCCCGCCGTATTAGTCTAGAGC
(forward)
and (SEQ ID NO: 31)
5' GCTCTAGACTAATACGGCGGGCCGCACGCCTCCGTCTT

CCCCGACGCACCCGGCCACAACCGCCACCGACCCCCCTTCC

CCCAATCGCATTCTGCAGGTACCCCG
(reverse).
```

This added several flanking amino acids from the phage coat sequence at either end of the 20 amino acid insert, such that the sequence around the insert site (beginning at the Kpn I site in pHisThioC) was PAEC-insert (DWGKGGRWRLW-PGASGKTEA)-GPPY- (SEQ ID NO:32) stop. X1-Blue bacteria were transformed with plasmid either containing insert (pThio-$A\beta$) or lacking insert (pThio). Transformed bacteria were grown and protein induced with 1 mM IPTG in log phase. Cells were pelleted and harvested by repeated cycles of freezing and thawing with subsequent sonication. Recombinant Thio or Thio-$A\beta$ protein was purified by incubation with ProBond nickel chelating resin (Invitrogen; Carlsbad, Calif.). Protein was bound with pH 7.8 buffer, washed successively with pH 6.0 and pH 5.5 buffers, and eluted with pH 4.0 buffer according to the manufacturer's instructions. Eluted protein was immediately re-pHed to 7.5 after elution. Recombinant protein comprised ca. 80% of the protein in fractions used for binding studies.

Binding assays with recombinant Thio and Thio-$A\beta$ protein and synthetic peptides: $A\beta_{1-40}$ was immobilized on 96-well ELISA plates as described above for phage panning. Immobilized $A\beta_{1-40}$ was blocked in phage panning buffer (Hanks balanced salts with 1 mM $CaCl_2$ and 1 mM $MgCl_2$, 10 mM Hepes, pH 7.4, and 0.5% BSA) for one hour. Thio or Thio-$A\beta$ protein was added at varying concentrations in phage panning buffer for 2 hours at room temperature. Plates were extensively washed in phage panning buffer without BSA. Anti-Thio antibody (Invitrogen; Carlsbad, Calif.) was added for 30 minutes in phage panning buffer at a dilution of 1:500. After washing, anti-mouse IgG conjugated to alkaline phosphatase was added at 1:500 for 40 minutes. Plates were washed again and incubated with paranitrophenyl phosphate (Sigma; St. Louis, Mo.). Developing substrate was read several times at 405 nm on an ELISA plate reader over the linear range (OD 0.2-1.0) and normalized to the highest binding signal. To calculate dissociation constants, binding curves were fitted by non-linear regression analysis assuming a single class of equivalent binding sites. Binding of primary and secondary antibody to $A\beta_{1-40}$ never exceeded 10% of the maximal signal for Thio-$A\beta$ in any experiment, and Thio protein never bound significantly above primary and secondary antibody alone at any concentration below 100 µM. Thio did show some binding in the mM range. By contrast, Thio-$A\beta$ protein was saturating at 200 nM.

For binding to synthetic peptides, two peptides were synthesized and purified containing an N-terminal biotin. One of these was the 20 amino acid-insert without any flanking sequences, Biotin-DWGKGGRWRLWPGASGKTEA (SEQ ID NO:2). The other sequence, Biotin-AECDWGKGGR-WRLWPGASGKTEACGP (SEQ ID NO:4), contained flanking cysteine residues and several other amino acids from the bacterial coat sequence. These peptides were purified by HPLC and confirmed by mass spectrometry to be over 90% pure. Peptides were solubilized in phage buffer and incubated at varying concentrations with $A\beta_{1-40}$ amyloid for 1 hour. After washing in phage buffer as above, streptavidin conjugated to alkaline phosphatase was added at 1 U/ml for 50 minutes. Plates or slides were washed extensively in phage buffer and developed, as above.

Staining of human brain with recombinant Thio-$A\beta$-protein and synthetic peptides: Normal and AD brain samples were obtained from the UCSD Alzheimer's Research Center (La Jolla, Calif.). Sections from a non-AD amyloidosis patient were obtained from the Department of Pathology (UCSD). Paraffin-embedded samples of cortex or other tissues were sectioned at 10 µm and mounted on glass slides. After deparifinization, sections were fixed in formic acid, blocked in phage panning buffer, and incubated with 5-500 nM Thio-$A\beta$ or Thio for two hours at room temperature. Binding was determined by subsequent staining with anti-Thio antibody and anti-mouse IgG coupled to alkaline phosphatase as above. After washing, staining was developed using 5-bromo-4-chloro-3-indolyl-phosphate and nitroblue tetrazolium for identical periods of time. All washes and incubations were done in phage buffer. The existence of amyloid plaques was confirmed by binding of anti-$A\beta$ monoclonal antibody (2066) to sections from the same brain samples. No significant staining was ever observed with secondary antibody alone. Background staining was allowed to develop to the point where cells in the section were evident. Staining with Thio-$A\beta$ was confirmed in brains from multiple AD subjects and was negative in multiple non-AD controls.

For staining with synthetic peptide, tissue sections from AD and non-AD brain, as well as from brain, kidney, small bowel, large bowel, and prostate from a non-AD patient with amyloidosis, were cut and prepared as above. Biotinylated peptide (AECDWGKGGRWRLWPGASGKTEACGP) (SEQ ID NO:4) was added in phage buffer for 1 hour at concentrations ranging from 0.1-10 µM. Sections were washed with phage buffer, incubated with streptavidin coupled to alkaline phosphatase, washed and developed as above. Positive staining of peptide to plaques in AD brain (and negative staining of non-$A\beta$ amyloid) was confirmed by simultaneous staining of sections using the same reagents. Congo Red or hematoxylin and eosin staining was done to confirm the presence of amyloid in amyloidosis sections.

Uptake by Neuronal Tissue: The peptides disclosed herein are hydrophobic, have a compact tertiary structure, and bind to the amyloid form of $A\beta_{1-40}$. In addition, the peptides cross the blood-brain barrier efficiently (see FIG. 8).

100 µL of a 1 mg/mL solution of amyloid binding-peptide (biotin-AECDWGKGGRWRLWPGASGKTEACGP (SEQ ID NO:4)) or control peptide without cysteines (biotin-DWGKGGRWRLWPGASGKTEA (SEQ ID NO:2)) was injected via the tail vein into 8-9 month old wild type CB6 mice. Peptides were injected in sterile Tris-buffered saline, pH 7.4, with 1 mM $CaCl_2$ and 1 mM $MgCl_2$. 4 animals were injected for each condition. Animals were then sacrificed after one minute or two minutes. Immediately upon sacrifice, blood and organs were harvested. To quantitate peptide uptake, brain, liver, and kidney were washed and the tissues lysed by homogenization in doubly distilled water. Organs and blood were centrifuged at 13000 g to collect lysate. Organ lysates or serum were then immobilized on ELISA plates that had been coated with nitrocellulose. Some tissue and serum samples were spiked with known amounts of purified peptide to verify levels of peptide immobilization in different sample types. For histochemical detection of biotinylated peptides in brain, a portion of the brain from each experiment was dissected and fixed for one day in 4% paraformaldehyde. These tissues were then dehydrated in PBS with varying levels of sucrose, frozen, and sectioned as described in Hoyte et al. (Brain Research: Molecular Brain Research 109:146-160 (2002)). 8 mm brain sections were stained for biotinylated peptide by binding of alkaline phosphatase-conjugated streptavidin. Levels of streptavidin binding were determined by development of sections in nitroblue tetrazolium and 5-bromo-4-chloro-3-indolyl phosphate. The levels of biotinylated peptide immobilized on ELISA plates was quantitated by binding of alkaline phosphatase-conjugated streptavidin. Levels of streptavidin binding were determined by development with para-nitrophenylphosphate, as in Kang et al. (Neurobiology of Disease 14:146-156 (2003)).

Figure 8:
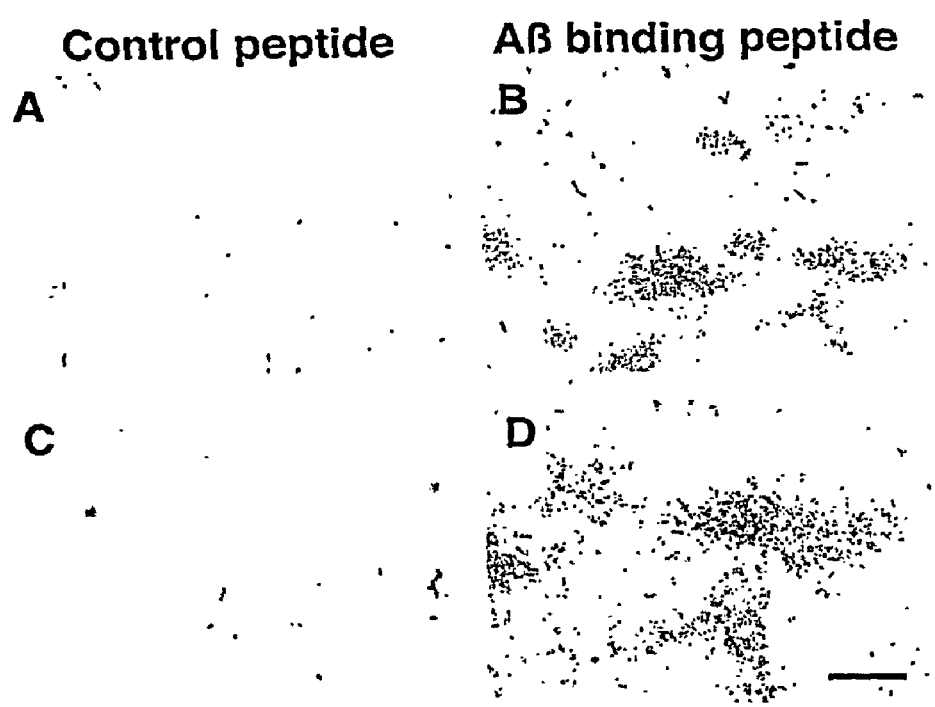
FIG. 8 depicts entry of amyloid binding peptide into the brain after intravenous injection.

Results of the rate of uptake, per minute, as a percentage relative to the amount of peptide in serum, is provided in Table 2 and FIG. 8. The amyloid binding peptide crossed the blood brain barrier into the brain parenchyma at a rate that was equivalent to that measured in kidney and at a rate that exceeded uptake into the liver.

In contrast, non-disulfide containing control peptide did not cross the blood-brain barrier. Access of the amyloid binding peptide was confirmed by immunostaining of sagittal sections of the brain. Here, both white and grey matter were positively stained, while the control peptide lacking cysteines only stained blood vessels (FIG. 8). These results indicate that the amyloid binding peptides disclosed herein can enter the brain.

The data demonstrate a practical way in which the peptides of the invention can be utilized as diagnostic or therapeutic agent in patients that have, or are at risk to develop, Alzheimer's disease. The fact that a rather large side chain, biotin, can be coupled to the peptide and that this does not create a barrier to brain uptake demonstrates the utility of this peptide to deliver conjugated agents. Such agents could be contrast agents to allow imaging of amyloid plaques, such as gadolinium, which would allow imaging by MRI, or therapeutic agents.

As indicated by the data presented in Table 2, one could achieve therapeutic and/or diagnostic concentrations of a peptide of the invention in the brain within 5 minutes by injecting 5-28 µg of peptide in the mouse or 3.7-21 mg of peptide in humans intravenously. This calculation assumes a cerebrospinal fluid volume of 200 µl in the mouse and 150 ml in the human. This is very practical amount of material that could be synthesized on a commercial scale. Thus, the robust nature of the uptake of this peptide into the brain should allow concentrations to be reached that would identify amyloid plaques. In addition, the robust nature of its uptake into the brain should allow for considerable flexibility in the types of reagents with which it could be modified.

FIG. 1 shows staining of amyloid $A\beta_{1-40}$ by phage peptides. Both phage peptide sequences selected for $A\beta_{1-40}$ amyloid binding stained amyloid deposits in vitro. Final clones 2 and 4 are the DWGKGGRWRLWPGASGKTEA (SEQ ID NO:2) sequence. This sequence identified both small and large (0.5-50 µm) accumulations of Aβ1-40 amyloid. Final clone 6 is the PGRSPFTGKKLFNQEFSQDQ (SEQ ID NO:3) sequence. This sequence stained $A\beta_{1-40}$ amyloid aggregates more poorly, but still stained well above background levels. None of the ten starting clones randomly picked (Starting clone 6 is shown) stained when used at the same concentration.

FIG. 2 shows immunoblotting of monomeric $A\beta_{1-40}$ by phage peptides. Monomeric $A\beta_{1-40}$ was separated on a 4-12% Bis/Tris gradient gel and blotted with either anti-Aβ antibody or with phage clones. No starting or final phage peptide clones recognized monomeric $A\beta_{1-40}$ peptide. Blotting with a monoclonal antibody that recognizes $A\beta_{1-40}$ is shown as a control for protein transfer.

FIG. 3 shows recombinant Aβ-binding peptide binds with high affinity to $A\beta_{1-40}$ amyloid in vitro. A recombinant cysteine-linked form of the DWGKGGRWRLWPGASGKTEA (SEQ ID NO2) sequence was produced as a fusion protein with thioredoxin in *E. coli* (Thio-Aβ). Recombinant Thio-Aβ was purified and binding to $A\beta_{1-40}$ amyloid was measured. Recombinant Thio-Aβ bound $A\beta_{1-40}$ amyloid with a Kd of 60 nM. Binding was saturating by 200 nM. Recombinant purified thioredoxin (Thio) showed no binding at any of the concentrations used. Errors are SEM for n=6.

Figure 4:
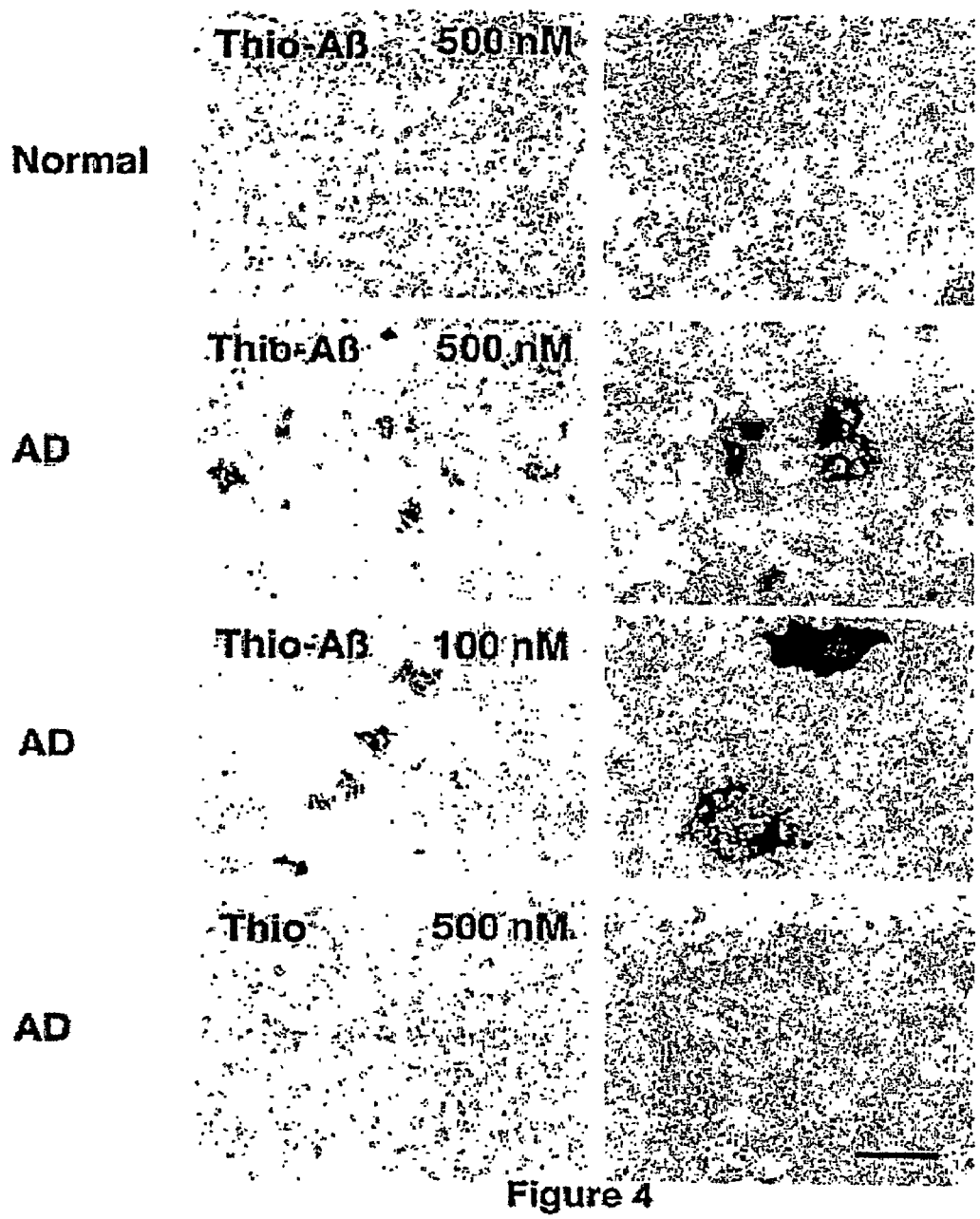
FIG. 4 depicts specific binding of Thio-Aβ to amyloid plaques in Alzheimer's disease brain.

FIG. 4 shows specific binding of Thio-Aβ to amyloid plaques in Alzheimer's disease brain. Recombinant Aβ-binding peptide conjugated to thioredoxin (Thio-Aβ) was used to stain brain samples from normal subjects and those with Alzheimer's disease (AD). Thio-Aβ did not stain any structures in normal brain tissue, but heavily stained amyloid plaques from AD brains. Background staining was allowed to increase to allow visualization of cells within the section, but this staining was not caused by Thio-Aβ. Thioredoxin (Thio) did not stain amyloid plaques in AD brains when added at the same concentrations. Bar is 100 µm for panels on the left and 25 µm for panels on the right.

FIG. 5 shows binding of synthetic peptides to $A\beta_{1-40}$ amyloid in vitro. Two biotin-labeled peptides, Biotin-DWGKGGRWRLWPGASGKTEA (SEQ ID NO:2) and Biotin-AECDWGKGGRWRLWPGASGKTEACGP (SEQ ID NO:4), were tested for binding to $A\beta_{1-40}$ amyloid. The peptide containing flanking cysteines bound with a Kd of 320 nM, while the peptide lacking these cysteines did not bind with significant affinity below 5 µM. Errors are SEM for n=6.

FIG. 6 shows specific staining amyloid plaques in Alzheimer's disease brain with a synthetic peptide. The Biotin-AECDWGKGGRWRLWPGASGKTEACGP (SEQ ID NO:4) peptide was used to stain brain sections from normal and AD brain. This peptide specifically stained amyloid plaques in AD brain. The peptide did not stain non-Aβ amyloid in tissues from a patient with amyloidosis (kidney is shown). Bar is 100 µm for panels on the left and 25 µm for panels on the right.

Figure 7:
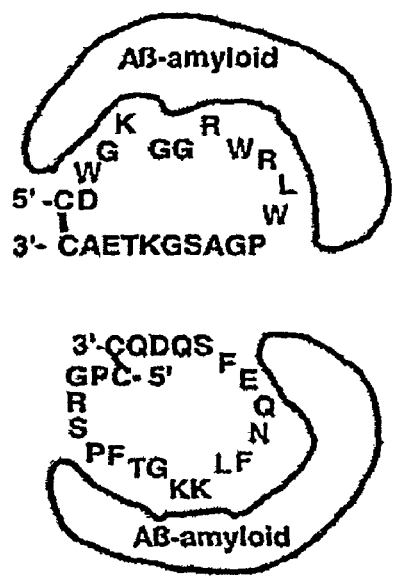
FIG. 7 depicts a model of uses for the $A\beta_{1-40}$ binding-peptides.

FIG. 7 shows a model of how Aβ1-40 binding-peptides can be used. The cysteine-linked peptide sequences CDWKGGRWRLWPGASGKTEAC (SEQ ID NO:5) and CPGRSPFTGKKLFNQEFSQDQC(SEQ ID NO:6) can be used to bind to amyloid plaques in Alzheimer's disease brain. These peptides could be used as carriers to deliver molecules to amyloid plaques that 1) lessen their neurotoxicity, 2) stimulate their destruction, or 3) inhibit their formation. In addition, such peptides could be conjugated to molecules used to 4) visualize amyloid plaques, or 5) induce an anti-idiotype antibody.

FIG. 8 depicts entry of amyloid binding peptide into the brain after intravenous injection. Amyloid binding peptide (biotin-AECDWGKGGRWRLWPGASGKTEACGP (SEQ ID NO:4)) was compared to binding of a control peptide lacking cysteines (biotin-DWGKGGRWRLWPGASGK-TEA (SEQ ID NO:2)) 2 minutes after intravenous injection via the tail vein in wild type mice. Control peptide was present in some blood vessels, but did not enter the brain parenchyma. Amyloid binding peptide, by contrast, entered the brain parenchyma in large amounts. Sagittal section of cortex is shown. The bar indicates 100 mm in A, B, 50 mm in C, D.

Table 1: Identification of peptides that adhere to $A\beta_{1-40}$ amyloid. A random 20-amino acid cysteine-cross-linked phage peptide library with $5\times10^7$ possible sequences was screened for adhesion to $A\beta_{1-40}$ amyloid. Sequences of 10 randomly picked phage clones in the starting library are shown, as are sequences of 10 randomly picked phage clones isolated after three rounds of panning against $A\beta_{1-40}$ amyloid. At least two peptides adhered to $A\beta_{1-40}$ amyloid. These sequences shared a density of similarly spaced bulky hydrophobic amino acids (underlined) that were not present in clones picked from the starting library. Two positively charged amino acids (dark) were present between the first two hydrophobic residues in both peptides.

Random Starting Clone Sequences:

```
1.   LGSGRIGDGWSDGGLARRLK     (SEQ ID NO: 7)
2.   DGGGGAGRWTTKDRSAAKTE     (SEQ ID NO: 8)
3.   VDDGAQGKRWGGMGLGKGRR     (SEQ ID NO: 9)
4.   SGSGVGLRMASQRHEGRKVY     (SEQ ID NO: 10)
5.   QLPQNGGPAWFTRKAGQGGR     (SEQ ID NO: 11)
6.   LGYAGGGQGMVEGSFWPTSW     (SEQ ID NO: 12)
7.   GLRGMEGRGYPKDRRDRNLE     (SEQ ID NO: 13)
8.   LIGGNKAGRGAWGVVASSGR     (SEQ ID NO: 14)
9.   ELESRGGLGYAWRGSASTMD     (SEQ ID NO: 15)
10.  KGETGNGGRAKAGTVDLIRR     (SEQ ID NO: 16)
```

Random Final Clone Sequences:

```
1.   DWGKGGRWRLWPGASGKTEA     (SEQ ID NO: 2)
2.   DWGKGGRWRLWPGASGKTEA     (SEQ ID NO: 2)
3.   DWGKGGRWRLWPGASGKTEA     (SEQ ID NO: 2)
4.   DWGKGGRWRLWPGASGKTEA     (SEQ ID NO: 2)
5.   DWGKGGRWRLWPGASGKTEA     (SEQ ID NO: 2)
6.   PGRSPFTGKKLFNQEFSQDQ     (SEQ ID NO: 3)
7.   DWGKGGRWRLWPGASGKTEA     (SEQ ID NO: 2)
8.   PGRSPFTGKKLFNQEFSQDQ     (SEQ ID NO: 3)
9.   DWGKGGRWRLWPGASGKTEA     (SEQ ID NO: 2)
10.  DWGKGGRWRLWPGASGKTEA     (SEQ ID NO: 2)
```

Table 2: Rate of uptake of amyloid binding peptide in brain, kidney, and liver. The rate of uptake of amyloid binding peptide was quantitated as a percentage of the concentration delivered intravenously into serum and compared to that for a non-cysteine containing control peptide. Only the amyloid binding peptide containing cysteines was delivered into the brain at a significant rate, and was equivalent to the rate of uptake into the kidney or the liver. Errors are SD for n=4.

| Organ | Peptide (SEQ ID NO:) | % uptake/min |
|---|---|---|
| Brain | biotin-AECDWGKGGRWRLWPGASGKTEACGP (4) | 0.18 .+−. 0.02% |
| Liver | biotin-AECDWGKGGRWRLWPGASGKTEACGP (4) | 0.06 .+−. 0.02% |
| Kidney | biotin-AECDWGKGGRWRLWPGASGKTEACGP (4) | 0.16 .+−. 0.02% |
| Brain | biotin-DWGKGGRWRLWPGASGKTEA (2) | 0.00005 .+−. 0.00005% |

It will be readily apparent to one skilled in the art that varying substitutions and modifications may be made to the invention disclosed herein without departing from the scope and spirit of the invention. Thus, such additional embodiments are within the scope of the present invention and the following claims.

The invention claimed is:

1. An antibody that binds to a polypeptide consisting of the amino acid sequence as set forth in SEQ ID NO:5.

2. An antibody that binds to a polypeptide comprising the amino acid sequence as set forth in SEQ ID NO:5, wherein the antibody specifically binds to epitopes within the amino acid sequence of SEQ ID NO:5.

3. The antibody of claim 1 or 2, that binds to a polypeptide comprising the amino acid sequence as set forth in SEQ ID NO:4, wherein the antibody specifically binds to epitopes within the amino acid sequence of SEQ ID NO:4.

4. The antibody of claim 3, that binds to a polypeptide consisting of the amino acid sequence as set forth in SEQ ID NO:4.

5. The antibody of claim 3, wherein the polypeptide comprising the amino acid sequence as set forth in SEQ ID NO:4 further comprises from one to twenty additional amino acids at the N-terminus, wherein the antibody specifically binds to epitopes within the amino acid sequence of SEQ ID NO:4.

* * * * *

SEQUENCE LISTING

```
<160> NUMBER OF SEQ ID NOS: 33

<210> SEQ ID NO 1
<211> LENGTH: 11
<212> TYPE: PRT
<213> ORGANISM: Artificial sequence
<220> FEATURE:
<223> OTHER INFORMATION: consensus peptide sequence
<220> FEATURE:
```

```
<221> NAME/KEY: MISC_FEATURE
<222> LOCATION: (1)..(1)
<223> OTHER INFORMATION: Xaa is W or F
<220> FEATURE:
<221> NAME/KEY: MISC_FEATURE
<222> LOCATION: (2)..(2)
<223> OTHER INFORMATION: Xaa is any amino acid that is not negatively
      charged
<220> FEATURE:
<221> NAME/KEY: MISC_FEATURE
<222> LOCATION: (3)..(3)
<223> OTHER INFORMATION: Xaa is a positively charged amino acid
<220> FEATURE:
<221> NAME/KEY: MISC_FEATURE
<222> LOCATION: (4)..(4)
<223> OTHER INFORMATION: Xaa is any amino acid that is not negatively
      charged
<220> FEATURE:
<221> NAME/KEY: MISC_FEATURE
<222> LOCATION: (5)..(5)
<223> OTHER INFORMATION: Xaa is any amino acid that is not negatively
      charged
<220> FEATURE:
<221> NAME/KEY: MISC_FEATURE
<222> LOCATION: (6)..(6)
<223> OTHER INFORMATION: Xaa is a postively charged amino acid
<220> FEATURE:
<221> NAME/KEY: MISC_FEATURE
<222> LOCATION: (7)..(7)
<223> OTHER INFORMATION: Xaa is W or F
<220> FEATURE:
<221> NAME/KEY: MISC_FEATURE
<222> LOCATION: (8)..(8)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is any amino acid
<220> FEATURE:
<221> NAME/KEY: MISC_FEATURE
<222> LOCATION: (10)..(10)
<223> OTHER INFORMATION: Xaa may or may not be present if Xaa is
      present Xaa is any amino acid
<220> FEATURE:
<221> NAME/KEY: MISC_FEATURE
<222> LOCATION: (11)..(11)
<223> OTHER INFORMATION: Xaa is W or F

<400> SEQUENCE: 1

Xaa Xaa Xaa Xaa Xaa Xaa Xaa Xaa Xaa Xaa Xaa
1               5                   10

<210> SEQ ID NO 2
<211> LENGTH: 20
<212> TYPE: PRT
<213> ORGANISM: Artificial sequence
<220> FEATURE:
<223> OTHER INFORMATION: Phage display peptide library sequence

<400> SEQUENCE: 2

Asp Trp Gly Lys Gly Gly Arg Trp Arg Leu Trp Pro Gly Ala Ser Gly
1               5                   10                  15

Lys Thr Glu Ala
            20

<210> SEQ ID NO 3
<211> LENGTH: 20
<212> TYPE: PRT
<213> ORGANISM: Artificial sequence
<220> FEATURE:
<223> OTHER INFORMATION: Phage display peptide library sequence

<400> SEQUENCE: 3

Pro Gly Arg Ser Pro Phe Thr Gly Lys Lys Leu Phe Asn Gln Glu Phe
```

```
                1               5                  10                 15
Ser Gln Asp Gln
            20

<210> SEQ ID NO 4
<211> LENGTH: 26
<212> TYPE: PRT
<213> ORGANISM: Artificial sequence
<220> FEATURE:
<223> OTHER INFORMATION: Phage display peptide library sequence

<400> SEQUENCE: 4

Ala Glu Cys Asp Trp Gly Lys Gly Gly Arg Trp Arg Leu Trp Pro Gly
1               5                  10                 15

Ala Ser Gly Lys Thr Glu Ala Cys Gly Pro
            20                  25

<210> SEQ ID NO 5
<211> LENGTH: 22
<212> TYPE: PRT
<213> ORGANISM: Artificial sequence
<220> FEATURE:
<223> OTHER INFORMATION: Phage display peptide library sequence

<400> SEQUENCE: 5

Cys Asp Trp Gly Lys Gly Gly Arg Trp Arg Leu Trp Pro Gly Ala Ser
1               5                  10                 15

Gly Lys Thr Glu Ala Cys
            20

<210> SEQ ID NO 6
<211> LENGTH: 22
<212> TYPE: PRT
<213> ORGANISM: Artificial sequence
<220> FEATURE:
<223> OTHER INFORMATION: Phage display peptide library sequence

<400> SEQUENCE: 6

Cys Pro Gly Arg Ser Pro Phe Thr Gly Lys Lys Leu Phe Asn Gln Glu
1               5                  10                 15

Phe Ser Gln Asp Gln Cys
            20

<210> SEQ ID NO 7
<211> LENGTH: 20
<212> TYPE: PRT
<213> ORGANISM: Artificial sequence
<220> FEATURE:
<223> OTHER INFORMATION: Phage display peptide library sequence

<400> SEQUENCE: 7

Leu Gly Ser Gly Arg Ile Gly Asp Gly Trp Ser Asp Gly Gly Leu Ala
1               5                  10                 15

Arg Arg Leu Lys
            20

<210> SEQ ID NO 8
<211> LENGTH: 20
<212> TYPE: PRT
<213> ORGANISM: Artificial sequence
<220> FEATURE:
<223> OTHER INFORMATION: Phage display peptide library sequence

<400> SEQUENCE: 8

Asp Gly Gly Gly Gly Ala Gly Arg Trp Thr Thr Lys Asp Arg Ser Ala
```

```
                1               5                  10                 15
Ala Lys Thr Glu
            20

<210> SEQ ID NO 9
<211> LENGTH: 20
<212> TYPE: PRT
<213> ORGANISM: Artificial sequence
<220> FEATURE:
<223> OTHER INFORMATION: Phage display peptide library sequence

<400> SEQUENCE: 9

Val Asp Asp Gly Ala Gln Gly Lys Arg Trp Gly Gly Met Gly Leu Gly
1               5                  10                 15

Lys Gly Arg Arg
            20

<210> SEQ ID NO 10
<211> LENGTH: 20
<212> TYPE: PRT
<213> ORGANISM: Artificial sequence
<220> FEATURE:
<223> OTHER INFORMATION: Phage display peptide library sequence

<400> SEQUENCE: 10

Ser Gly Ser Gly Val Gly Leu Arg Met Ala Ser Gln Arg His Glu Gly
1               5                  10                 15

Arg Lys Val Tyr
            20

<210> SEQ ID NO 11
<211> LENGTH: 20
<212> TYPE: PRT
<213> ORGANISM: Artificial sequence
<220> FEATURE:
<223> OTHER INFORMATION: Phage display peptide library sequence

<400> SEQUENCE: 11

Gln Leu Pro Gln Asn Gly Gly Pro Ala Trp Phe Thr Arg Lys Ala Gly
1               5                  10                 15

Gln Gly Gly Arg
            20

<210> SEQ ID NO 12
<211> LENGTH: 20
<212> TYPE: PRT
<213> ORGANISM: Artificial sequence
<220> FEATURE:
<223> OTHER INFORMATION: Phage display peptide library sequence

<400> SEQUENCE: 12

Leu Gly Tyr Ala Gly Gly Gly Gln Gly Met Val Glu Gly Ser Phe Trp
1               5                  10                 15

Pro Thr Ser Trp
            20

<210> SEQ ID NO 13
<211> LENGTH: 20
<212> TYPE: PRT
<213> ORGANISM: Artificial sequence
<220> FEATURE:
<223> OTHER INFORMATION: Phage display peptide library sequence

<400> SEQUENCE: 13

Gly Leu Arg Gly Met Glu Gly Arg Gly Tyr Pro Lys Asp Arg Arg Asp
```

```
                1               5                   10                  15

Arg Asn Leu Glu
            20

<210> SEQ ID NO 14
<211> LENGTH: 20
<212> TYPE: PRT
<213> ORGANISM: Artificial sequence
<220> FEATURE:
<223> OTHER INFORMATION: Phage display peptide library sequence

<400> SEQUENCE: 14

Leu Ile Gly Gly Asn Lys Ala Gly Arg Gly Ala Trp Gly Val Val Ala
1               5                   10                  15

Ser Ser Gly Arg
            20

<210> SEQ ID NO 15
<211> LENGTH: 20
<212> TYPE: PRT
<213> ORGANISM: Artificial sequence
<220> FEATURE:
<223> OTHER INFORMATION: Phage display peptide library sequence

<400> SEQUENCE: 15

Glu Leu Glu Ser Arg Gly Gly Leu Gly Tyr Ala Trp Arg Gly Ser Ala
1               5                   10                  15

Ser Thr Met Asp
            20

<210> SEQ ID NO 16
<211> LENGTH: 20
<212> TYPE: PRT
<213> ORGANISM: Artificial sequence
<220> FEATURE:
<223> OTHER INFORMATION: Phage display peptide library sequence

<400> SEQUENCE: 16

Lys Gly Glu Thr Gly Asn Gly Gly Arg Ala Lys Ala Gly Thr Val Asp
1               5                   10                  15

Leu Ile Arg Arg
            20

<210> SEQ ID NO 17
<211> LENGTH: 50
<212> TYPE: PRT
<213> ORGANISM: Artificial sequence
<220> FEATURE:
<223> OTHER INFORMATION: Consensus peptide sequence
<220> FEATURE:
<221> NAME/KEY: MISC_FEATURE
<222> LOCATION: (1)..(20)
<223> OTHER INFORMATION: Xaa may or may not be present.  If present, Xaa
      can be any amino acid, preferably C.
<220> FEATURE:
<221> NAME/KEY: MISC_FEATURE
<222> LOCATION: (21)..(21)
<223> OTHER INFORMATION: Xaa is W or F
<220> FEATURE:
<221> NAME/KEY: MISC_FEATURE
<222> LOCATION: (22)..(25)
<223> OTHER INFORMATION: Xaa is a positively charged or non-negatively
      charged amino acid
<220> FEATURE:
<221> NAME/KEY: MISC_FEATURE
<222> LOCATION: (26)..(26)
<223> OTHER INFORMATION: Xaa is a positively charged amino acid
<220> FEATURE:
<221> NAME/KEY: MISC_FEATURE
```

```
<222> LOCATION: (27)..(27)
<223> OTHER INFORMATION: Xaa is W or F
<220> FEATURE:
<221> NAME/KEY: MISC_FEATURE
<222> LOCATION: (28)..(28)
<223> OTHER INFORMATION: Xaa is any amino acid
<220> FEATURE:
<221> NAME/KEY: MISC_FEATURE
<222> LOCATION: (29)..(29)
<223> OTHER INFORMATION: Xaa is any amino acid
<220> FEATURE:
<221> NAME/KEY: MISC_FEATURE
<222> LOCATION: (30)..(30)
<223> OTHER INFORMATION: Xaa is W or F
<220> FEATURE:
<221> NAME/KEY: MISC_FEATURE
<222> LOCATION: (31)..(50)
<223> OTHER INFORMATION: Xaa may or may not be present.  If present, Xaa
      can be any amino acid, preferably C.

<400> SEQUENCE: 17

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa
    50

<210> SEQ ID NO 18
<211> LENGTH: 30
<212> TYPE: PRT
<213> ORGANISM: Artificial sequence
<220> FEATURE:
<223> OTHER INFORMATION: Consensus peptide sequence
<220> FEATURE:
<221> NAME/KEY: MISC_FEATURE
<222> LOCATION: (1)..(20)
<223> OTHER INFORMATION: Xaa may or may not be present.  If present, Xaa
      can be any amino acid, preferably C.
<220> FEATURE:
<221> NAME/KEY: MISC_FEATURE
<222> LOCATION: (21)..(21)
<223> OTHER INFORMATION: Xaa is W or F
<220> FEATURE:
<221> NAME/KEY: MISC_FEATURE
<222> LOCATION: (22)..(25)
<223> OTHER INFORMATION: Xaa is a positively charged or non-negatively
      charged amino acid
<220> FEATURE:
<221> NAME/KEY: MISC_FEATURE
<222> LOCATION: (26)..(26)
<223> OTHER INFORMATION: Xaa is a positively charged amino acid
<220> FEATURE:
<221> NAME/KEY: MISC_FEATURE
<222> LOCATION: (27)..(27)
<223> OTHER INFORMATION: Xaa is W or F
<220> FEATURE:
<221> NAME/KEY: MISC_FEATURE
<222> LOCATION: (28)..(29)
<223> OTHER INFORMATION: Xaa is any amino acid
<220> FEATURE:
<221> NAME/KEY: MISC_FEATURE
<222> LOCATION: (30)..(30)
<223> OTHER INFORMATION: Xaa is W or F

<400> SEQUENCE: 18

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa
            20                  25                  30
```

```
<210> SEQ ID NO 19
<211> LENGTH: 30
<212> TYPE: PRT
<213> ORGANISM: Artificial sequence
<220> FEATURE:
<223> OTHER INFORMATION: Consensus peptide sequence
<220> FEATURE:
<221> NAME/KEY: MISC_FEATURE
<222> LOCATION: (1)..(1)
<223> OTHER INFORMATION: Xaa is W or F
<220> FEATURE:
<221> NAME/KEY: MISC_FEATURE
<222> LOCATION: (2)..(5)
<223> OTHER INFORMATION: Xaa is a positively charged or non-negatively
      charged amino acid
<220> FEATURE:
<221> NAME/KEY: MISC_FEATURE
<222> LOCATION: (6)..(6)
<223> OTHER INFORMATION: Xaa is a positively charged amino acid
<220> FEATURE:
<221> NAME/KEY: MISC_FEATURE
<222> LOCATION: (7)..(7)
<223> OTHER INFORMATION: Xaa is W or F
<220> FEATURE:
<221> NAME/KEY: MISC_FEATURE
<222> LOCATION: (8)..(9)
<223> OTHER INFORMATION: Xaa is any amino acid
<220> FEATURE:
<221> NAME/KEY: MISC_FEATURE
<222> LOCATION: (10)..(10)
<223> OTHER INFORMATION: Xaa is W or F
<220> FEATURE:
<221> NAME/KEY: MISC_FEATURE
<222> LOCATION: (11)..(30)
<223> OTHER INFORMATION: Xaa may or may not be present.  If present, Xaa
      can be any amino acid, preferably C.

<400> SEQUENCE: 19

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa
            20                  25                  30

<210> SEQ ID NO 20
<211> LENGTH: 12
<212> TYPE: PRT
<213> ORGANISM: Artificial sequence
<220> FEATURE:
<223> OTHER INFORMATION: Consensus peptide sequence
<220> FEATURE:
<221> NAME/KEY: MISC_FEATURE
<222> LOCATION: (1)..(1)
<223> OTHER INFORMATION: Xaa may or may not be present.  If present, Xaa
      can be any amino acid, preferably C.
<220> FEATURE:
<221> NAME/KEY: MISC_FEATURE
<222> LOCATION: (2)..(2)
<223> OTHER INFORMATION: Xaa is W or F
<220> FEATURE:
<221> NAME/KEY: MISC_FEATURE
<222> LOCATION: (3)..(6)
<223> OTHER INFORMATION: Xaa is a positively charged or non-negatively
      charged amino acid
<220> FEATURE:
<221> NAME/KEY: MISC_FEATURE
<222> LOCATION: (7)..(7)
<223> OTHER INFORMATION: Xaa is a positively charged amino acid
<220> FEATURE:
<221> NAME/KEY: MISC_FEATURE
<222> LOCATION: (8)..(8)
<223> OTHER INFORMATION: Xaa is W or F
<220> FEATURE:
<221> NAME/KEY: MISC_FEATURE
<222> LOCATION: (9)..(10)
<223> OTHER INFORMATION: Xaa is any amino acid
<220> FEATURE:
```

```
<221> NAME/KEY: MISC_FEATURE
<222> LOCATION: (11)..(11)
<223> OTHER INFORMATION: Xaa is W or F
<220> FEATURE:
<221> NAME/KEY: MISC_FEATURE
<222> LOCATION: (12)..(12)
<223> OTHER INFORMATION: Xaa may or may not be present.  If present, Xaa
      can be any amino acid, preferably C.

<400> SEQUENCE: 20

Xaa Xaa Xaa Xaa Xaa Xaa Xaa Xaa Xaa Xaa Xaa Xaa
1               5                   10

<210> SEQ ID NO 21
<211> LENGTH: 51
<212> TYPE: PRT
<213> ORGANISM: Artificial sequence
<220> FEATURE:
<223> OTHER INFORMATION: Consensus peptide sequence
<220> FEATURE:
<221> NAME/KEY: MISC_FEATURE
<222> LOCATION: (1)..(20)
<223> OTHER INFORMATION: Xaa may or may not be present.  If present, Xaa
      can be any amino acid, preferably C.
<220> FEATURE:
<221> NAME/KEY: MISC_FEATURE
<222> LOCATION: (21)..(21)
<223> OTHER INFORMATION: Xaa is W or F
<220> FEATURE:
<221> NAME/KEY: MISC_FEATURE
<222> LOCATION: (22)..(22)
<223> OTHER INFORMATION: Xaa is a non-negatively charged amino acid
<220> FEATURE:
<221> NAME/KEY: MISC_FEATURE
<222> LOCATION: (23)..(23)
<223> OTHER INFORMATION: Xaa is a positively charged amino acid
<220> FEATURE:
<221> NAME/KEY: MISC_FEATURE
<222> LOCATION: (24)..(25)
<223> OTHER INFORMATION: Xaa is a non-negatively charged amino acid
<220> FEATURE:
<221> NAME/KEY: MISC_FEATURE
<222> LOCATION: (26)..(26)
<223> OTHER INFORMATION: Xaa is a positively charged amino acid
<220> FEATURE:
<221> NAME/KEY: MISC_FEATURE
<222> LOCATION: (27)..(27)
<223> OTHER INFORMATION: Xaa is W or F
<220> FEATURE:
<221> NAME/KEY: MISC_FEATURE
<222> LOCATION: (28)..(30)
<223> OTHER INFORMATION: Xaa is any amino acid
<220> FEATURE:
<221> NAME/KEY: MISC_FEATURE
<222> LOCATION: (31)..(31)
<223> OTHER INFORMATION: Xaa is W or F
<220> FEATURE:
<221> NAME/KEY: MISC_FEATURE
<222> LOCATION: (32)..(51)
<223> OTHER INFORMATION: Xaa may or may not be present.  If present, Xaa
      can be any amino acid, preferably C.

<400> SEQUENCE: 21

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa
    50

<210> SEQ ID NO 22
```

```
<211> LENGTH: 31
<212> TYPE: PRT
<213> ORGANISM: Artificial sequence
<220> FEATURE:
<223> OTHER INFORMATION: Consensus peptide sequence
<220> FEATURE:
<221> NAME/KEY: MISC_FEATURE
<222> LOCATION: (1)..(20)
<223> OTHER INFORMATION: Xaa may or may not be present.  If present, Xaa
      can be any amino acid, preferably C.
<220> FEATURE:
<221> NAME/KEY: MISC_FEATURE
<222> LOCATION: (21)..(21)
<223> OTHER INFORMATION: Xaa is W or F
<220> FEATURE:
<221> NAME/KEY: MISC_FEATURE
<222> LOCATION: (22)..(22)
<223> OTHER INFORMATION: Xaa is a non-negatively charged amino acid
<220> FEATURE:
<221> NAME/KEY: MISC_FEATURE
<222> LOCATION: (23)..(23)
<223> OTHER INFORMATION: Xaa is a positively charged amino acid
<220> FEATURE:
<221> NAME/KEY: MISC_FEATURE
<222> LOCATION: (24)..(25)
<223> OTHER INFORMATION: Xaa is a non-negatively charged amino acid
<220> FEATURE:
<221> NAME/KEY: MISC_FEATURE
<222> LOCATION: (26)..(26)
<223> OTHER INFORMATION: Xaa is a positively charged amino acid
<220> FEATURE:
<221> NAME/KEY: MISC_FEATURE
<222> LOCATION: (27)..(27)
<223> OTHER INFORMATION: Xaa is W or F
<220> FEATURE:
<221> NAME/KEY: MISC_FEATURE
<222> LOCATION: (28)..(30)
<223> OTHER INFORMATION: Xaa is any amino acid
<220> FEATURE:
<221> NAME/KEY: MISC_FEATURE
<222> LOCATION: (31)..(31)
<223> OTHER INFORMATION: Xaa is W or F

<400> SEQUENCE: 22

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

<210> SEQ ID NO 23
<211> LENGTH: 31
<212> TYPE: PRT
<213> ORGANISM: Artificial sequence
<220> FEATURE:
<223> OTHER INFORMATION: Consensus peptide sequence
<220> FEATURE:
<221> NAME/KEY: MISC_FEATURE
<222> LOCATION: (1)..(1)
<223> OTHER INFORMATION: Xaa is W or F
<220> FEATURE:
<221> NAME/KEY: MISC_FEATURE
<222> LOCATION: (2)..(2)
<223> OTHER INFORMATION: Xaa is a non-negatively charged amino acid
<220> FEATURE:
<221> NAME/KEY: MISC_FEATURE
<222> LOCATION: (3)..(3)
<223> OTHER INFORMATION: Xaa is a positively charged amino acid
<220> FEATURE:
<221> NAME/KEY: MISC_FEATURE
<222> LOCATION: (4)..(5)
<223> OTHER INFORMATION: Xaa is a non-negatively charged amino acid
<220> FEATURE:
<221> NAME/KEY: MISC_FEATURE
<222> LOCATION: (6)..(6)
<223> OTHER INFORMATION: Xaa is a positively charged amino acid
<220> FEATURE:
<221> NAME/KEY: MISC_FEATURE
```

```
<222> LOCATION: (7)..(7)
<223> OTHER INFORMATION: Xaa is W or F
<220> FEATURE:
<221> NAME/KEY: MISC_FEATURE
<222> LOCATION: (8)..(10)
<223> OTHER INFORMATION: Xaa is any amino acid
<220> FEATURE:
<221> NAME/KEY: MISC_FEATURE
<222> LOCATION: (11)..(11)
<223> OTHER INFORMATION: Xaa is W or F
<220> FEATURE:
<221> NAME/KEY: MISC_FEATURE
<222> LOCATION: (12)..(31)
<223> OTHER INFORMATION: Xaa may or may not be present.  If present, Xaa
      can be any amino acid, preferably C.

<400> SEQUENCE: 23

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
                20                  25                  30

<210> SEQ ID NO 24
<211> LENGTH: 11
<212> TYPE: PRT
<213> ORGANISM: Artificial sequence
<220> FEATURE:
<223> OTHER INFORMATION: Consensus peptide sequence
<220> FEATURE:
<221> NAME/KEY: MISC_FEATURE
<222> LOCATION: (1)..(1)
<223> OTHER INFORMATION: Xaa is W or F
<220> FEATURE:
<221> NAME/KEY: MISC_FEATURE
<222> LOCATION: (2)..(2)
<223> OTHER INFORMATION: Xaa is a non-negatively charged amino acid
<220> FEATURE:
<221> NAME/KEY: MISC_FEATURE
<222> LOCATION: (3)..(3)
<223> OTHER INFORMATION: Xaa is a positively charged amino acid
<220> FEATURE:
<221> NAME/KEY: MISC_FEATURE
<222> LOCATION: (4)..(5)
<223> OTHER INFORMATION: Xaa is a non-negatively charged amino acid
<220> FEATURE:
<221> NAME/KEY: MISC_FEATURE
<222> LOCATION: (6)..(6)
<223> OTHER INFORMATION: Xaa is a positively charged amino acid
<220> FEATURE:
<221> NAME/KEY: MISC_FEATURE
<222> LOCATION: (7)..(7)
<223> OTHER INFORMATION: Xaa is W or F
<220> FEATURE:
<221> NAME/KEY: MISC_FEATURE
<222> LOCATION: (8)..(10)
<223> OTHER INFORMATION: Xaa is any amino acid
<220> FEATURE:
<221> NAME/KEY: MISC_FEATURE
<222> LOCATION: (11)..(11)
<223> OTHER INFORMATION: Xaa is W or F

<400> SEQUENCE: 24

Xaa Xaa Xaa Xaa Xaa Xaa Xaa Xaa Xaa Xaa Xaa
1               5                   10

<210> SEQ ID NO 25
<211> LENGTH: 5
<212> TYPE: PRT
<213> ORGANISM: Artificial sequence
<220> FEATURE:
<223> OTHER INFORMATION: Flanking peptide sequence

<400> SEQUENCE: 25

Ser Arg Lys Asn Gln
```

<210> SEQ ID NO 26
<211> LENGTH: 9
<212> TYPE: PRT
<213> ORGANISM: Artificial sequence
<220> FEATURE:
<223> OTHER INFORMATION: Phage display peptide library sequence

<400> SEQUENCE: 26

His Cys Ser Gln Asn Glu Asp Gly Ala
1               5

<210> SEQ ID NO 27
<211> LENGTH: 9
<212> TYPE: PRT
<213> ORGANISM: Artificial sequence
<220> FEATURE:
<223> OTHER INFORMATION: Phage display peptide library sequence

<400> SEQUENCE: 27

Tyr Ser Thr Thr Ser Trp Tyr Tyr Trp
1               5

<210> SEQ ID NO 28
<211> LENGTH: 40
<212> TYPE: PRT
<213> ORGANISM: Artificial sequence
<220> FEATURE:
<223> OTHER INFORMATION: Alpha-Beta 1-40 fragment

<400> SEQUENCE: 28

Asp Ala Glu Phe Lys His Asp Ser Gly Thr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 29
<211> LENGTH: 20
<212> TYPE: DNA
<213> ORGANISM: Artificial sequence
<220> FEATURE:
<223> OTHER INFORMATION: primer

<400> SEQUENCE: 29
gtttgtcgtc tttccagacg                                           20

<210> SEQ ID NO 30
<211> LENGTH: 105
<212> TYPE: DNA
<213> ORGANISM: Artificial sequence
<220> FEATURE:
<223> OTHER INFORMATION: Nucleotide cloning sequence

<400> SEQUENCE: 30
cggggtacct gcagaatgcg attgggggaa ggggggtcgg tggcggttgt ggccgggtgc    60
gtcggggaag acggaggcgt gcggcccgcc gtattagtct agagc                   105

<210> SEQ ID NO 31
<211> LENGTH: 105
<212> TYPE: DNA
<213> ORGANISM: Artificial sequence
<220> FEATURE:
<223> OTHER INFORMATION: Nucleotide cloning sequence

```
<400> SEQUENCE: 31
gctctagact aatacggcgg gccgcacgcc tccgtcttcc ccgacgcacc cggccacaac      60
cgccaccgac cccccttccc ccaatcgcat tctgcaggta ccccg                    105

<210> SEQ ID NO 32
<211> LENGTH: 5
<212> TYPE: PRT
<213> ORGANISM: Artificial sequence
<220> FEATURE:
<223> OTHER INFORMATION: Flanking sequence from phage coat

<400> SEQUENCE: 32

Cys Gly Pro Pro Tyr
1               5

<210> SEQ ID NO 33
<211> LENGTH: 11
<212> TYPE: PRT
<213> ORGANISM: Artificial sequence
<220> FEATURE:
<223> OTHER INFORMATION: Consensus peptide sequence
<220> FEATURE:
<221> NAME/KEY: MISC_FEATURE
<222> LOCATION: (1)..(1)
<223> OTHER INFORMATION: Xaa is W or F
<220> FEATURE:
<221> NAME/KEY: MISC_FEATURE
<222> LOCATION: (2)..(6)
<223> OTHER INFORMATION: Xaa is any positively charged amino acid
<220> FEATURE:
<221> NAME/KEY: MISC_FEATURE
<222> LOCATION: (7)..(7)
<223> OTHER INFORMATION: Xaa is W or F
<220> FEATURE:
<221> NAME/KEY: MISC_FEATURE
<222> LOCATION: (8)..(10)
<223> OTHER INFORMATION: Xaa is any amino acid
<220> FEATURE:
<221> NAME/KEY: MISC_FEATURE
<222> LOCATION: (11)..(11)
<223> OTHER INFORMATION: Xaa is W or F

<400> SEQUENCE: 33

Xaa Xaa Xaa Xaa Xaa Xaa Xaa Xaa Xaa Xaa Xaa
1               5                   10
```